(12) United States Patent
Godhani et al.

(10) Patent No.: US 11,896,441 B2
(45) Date of Patent: Feb. 13, 2024

(54) SYSTEMS AND METHODS FOR MEASURING A DISTANCE USING A STEREOSCOPIC ENDOSCOPE

(71) Applicant: Intuitive Surgical Operations, Inc., Sunnyvale, CA (US)

(72) Inventors: Rohitkumar Godhani, Milpitas, CA (US); Brian D. Hoffman, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 753 days.

(21) Appl. No.: 17/051,515

(22) PCT Filed: May 2, 2019

(86) PCT No.: PCT/US2019/030455
§ 371 (c)(1),
(2) Date: Oct. 29, 2020

(87) PCT Pub. No.: WO2019/213432
PCT Pub. Date: Nov. 7, 2019

(65) Prior Publication Data
US 2021/0220078 A1 Jul. 22, 2021

Related U.S. Application Data

(60) Provisional application No. 62/666,505, filed on May 3, 2018.

(51) Int. Cl.
*A61B 90/00* (2016.01)
*A61B 34/20* (2016.01)
(Continued)

(52) U.S. Cl.
CPC .......... *A61B 90/36* (2016.02); *A61B 1/00193* (2013.01); *A61B 34/20* (2016.02);
(Continued)

(58) Field of Classification Search
CPC ..... A61B 90/36; A61B 1/00193; A61B 34/20; A61B 34/25; A61B 34/70;
(Continued)

(56) References Cited

U.S. PATENT DOCUMENTS

2006/0178561 A1 8/2006 Nakano et al.
2010/0166294 A1* 7/2010 Marrion ............... G06V 10/757
382/154

(Continued)

FOREIGN PATENT DOCUMENTS

KR 100264393 B1 8/2000
WO WO-2009085616 A1 7/2009

OTHER PUBLICATIONS

Extended European Search Report for Application No. EP19797023.9, dated Dec. 23, 2021, 12 pages.
Jason G., et al., "Review of 3-D Endoscopic Surface Imaging Techniques," IEEE Sensors Journal, IEEE, Apr. 1, 2014, vol. 14 (4), pp. 945-960.

(Continued)

*Primary Examiner* — Michael E Teitelbaum

(57) ABSTRACT

A measurement system accesses first and second images captured respectively from first and second vantage points by first and second cameras included within a stereoscopic endo scope located at a surgical area associated with a patient. The measurement system receives user input designating a user-selected two-dimensional ("2D") endpoint corresponding to a feature within the surgical area as represented in the first image, and identifies, based on the user-selected 2D endpoint, a matched 2D endpoint corresponding to the feature as represented in the second image. Based on the user-selected and matched 2D endpoints, the measurement system defines a three-dimensional ("3D") endpoint corresponding to the feature within the surgical area. The measurement system then determines a distance from the 3D endpoint to an additional 3D endpoint corre- (Continued)

sponding to an additional feature within the surgical area. Corresponding systems and methods are also described.

20 Claims, 16 Drawing Sheets

(51) Int. Cl.
    *A61B 34/00*     (2016.01)
    *A61B 1/00*     (2006.01)
    *A61B 34/30*     (2016.01)

(52) U.S. Cl.
    CPC .............. *A61B 34/25* (2016.02); *A61B 34/70* (2016.02); *A61B 2034/2046* (2016.02); *A61B 2034/301* (2016.02); *A61B 2090/364* (2016.02)

(58) Field of Classification Search
    CPC ...... A61B 2034/2046; A61B 2034/301; A61B 2090/364; A61B 2090/061; A61B 2090/367; A61B 34/37; A61B 34/30; G06T 2207/10012; G06T 2207/10068; G06T 2207/30004; G06T 7/60
    See application file for complete search history.

(56) References Cited

U.S. PATENT DOCUMENTS

| | | |
|---|---|---|
| 2013/0023732 A1* | 1/2013 | Kim .................. G02B 23/2461 600/166 |
| 2013/0113893 A1 | 5/2013 | Stevens et al. |
| 2015/0215614 A1 | 7/2015 | Witt |
| 2017/0061624 A1 | 3/2017 | Seshadrinathan et al. |
| 2018/0035966 A1* | 2/2018 | Merlet ...................... G06T 7/33 |

OTHER PUBLICATIONS

Stefano L.D., et al., "A Fast Area-Based Stereo Matching Algorithm," Image and Vision Computing, 2004, vol. 22, pp. 983-1005.

Traumann A., et al., "Accurate 3D Measurement Using Optical Depth Information," Electronics Letters, Sep. 3, 2015, vol. 51 (18), pp. 1420-1422.

International Search Report and Written Opinion for Application No. PCT/US2019/030455, dated Aug. 9, 2019, 10 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/030455, dated Nov. 12, 2020, 6 pages.

* cited by examiner

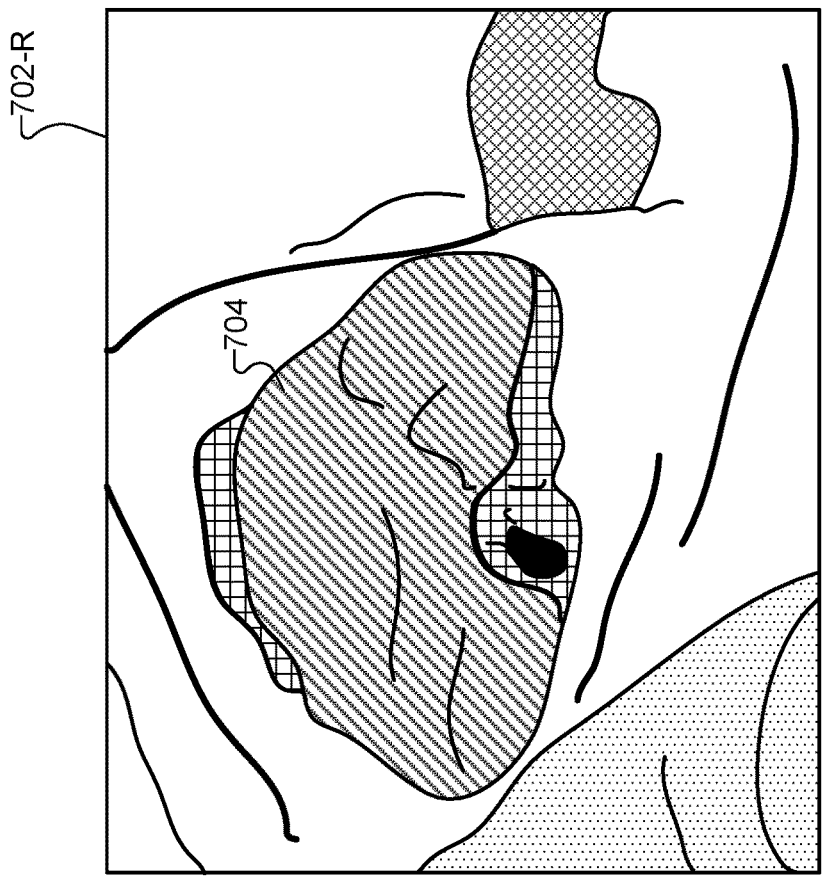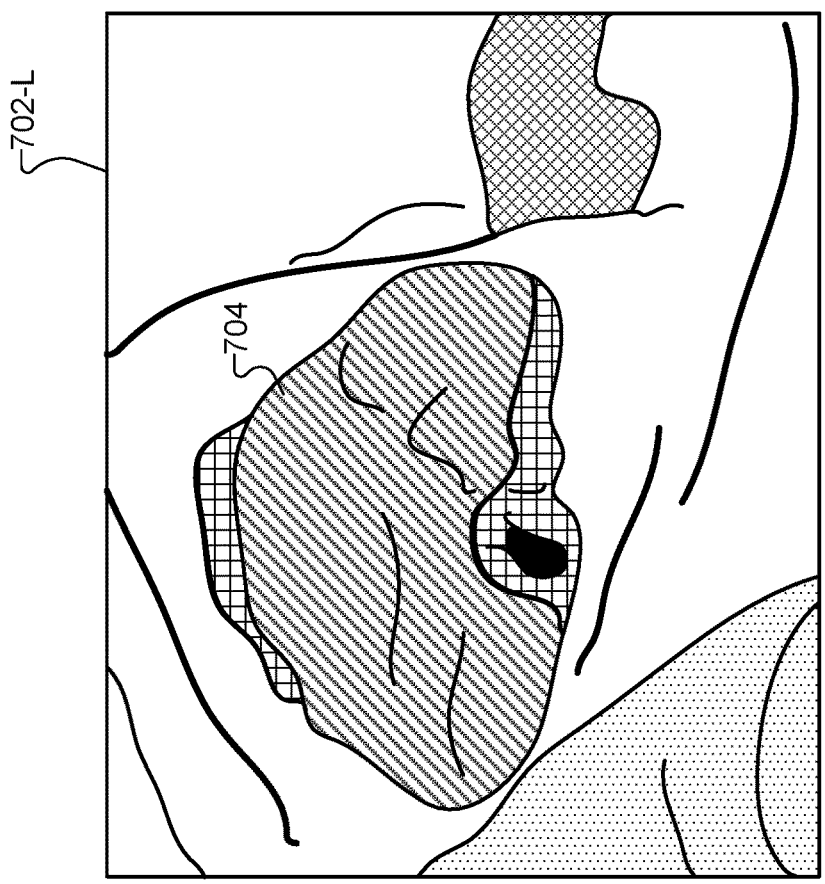
Fig. 7

Fig. 10

SYSTEMS AND METHODS FOR MEASURING A DISTANCE USING A STEREOSCOPIC ENDOSCOPE

RELATED APPLICATIONS

The present application claims priority to U.S. Provisional Patent Application No. 62/666,505, filed on May 3, 2018, and entitled "Systems and Methods for Measuring a Distance Using a Stereoscopic Endoscope," the contents of which are hereby incorporated by reference in their entirety.

BACKGROUND INFORMATION

During a minimally invasive surgical procedure, such as a procedure that utilizes a robotic surgical system, an endoscopic camera is typically used to provide images (e.g., stereoscopic video) of a patient's internal anatomy to a surgeon. While viewing these images, the surgeon may manipulate one or more surgical instruments (e.g., one or more robotically-manipulated surgical instruments) that are positioned within the patient to perform the procedure.

In some scenarios, it may be desirable to measure various distances associated with a patient's internal anatomy before, during, or after a minimally invasive surgical procedure. For example, it may be desirable to measure the size of a hernia within the patient so that a mesh patch may be appropriately sized to fit the hernia. As another example, it may be desirable to ascertain how far away a tip of a surgical instrument is from tissue within the patient.

Unfortunately, because the surgeon performing the minimally invasive surgical procedure does not have direct physical access to the patient's internal anatomy as he or she would during a conventional "open" surgical procedure, such measurements have heretofore been difficult or impossible to accurately ascertain. One approach for estimating a distance associated with a patient's internal anatomy during a minimally invasive surgical procedure has been to position robotically-manipulated surgical instruments at different positions within the patient and to approximate a distance between the instruments based on tracked kinematic data for the instruments. However, it may be inconvenient, difficult, and/or time consuming to position instruments in this way, and measurements resulting from this conventional approach may be somewhat inaccurate due to imprecision introduced over a relatively long kinematic chain. Additionally, it may not be possible to account for contours of surfaces between endpoints when using such conventional techniques. This may pose a problem for measurements, such as the exemplary hernia measurement described above, where accounting for such contours may be important.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 7 illustrates exemplary images captured from stereoscopic vantage points by cameras included within a stereoscopic endoscope according to principles described herein.

FIG. 10 illustrates a zoomed in, pixel-level view of certain aspects of the images illustrated in FIG. 9 according to principles described herein.

DETAILED DESCRIPTION

Figure 1:
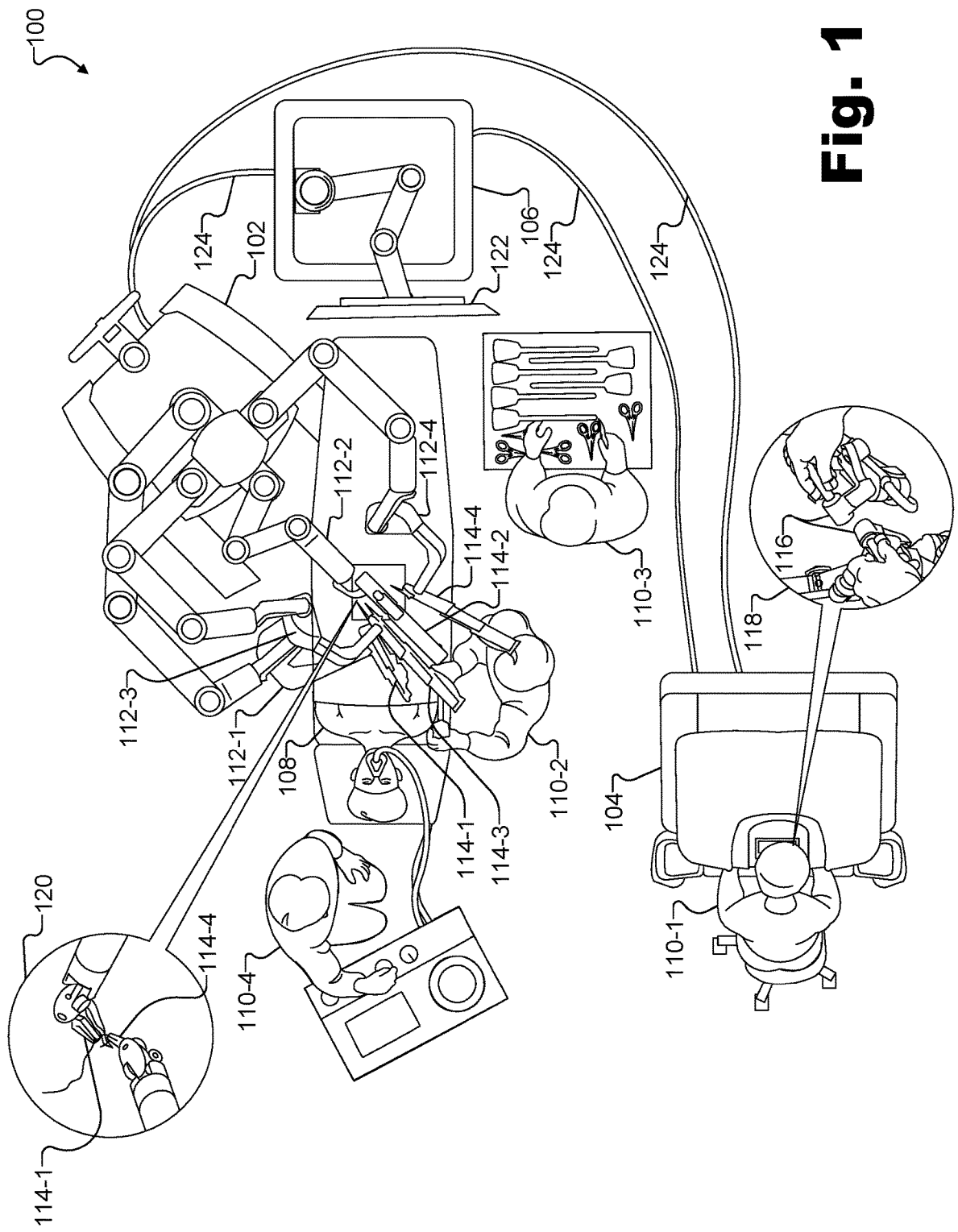
FIG. 1 illustrates an exemplary robotic surgical system according to principles described herein.

Systems and methods for measuring a distance using a stereoscopic endoscope are described herein. For example, in certain implementations, a measurement system may include at least one physical computing device (e.g., a processor programmed by instructions stored in a memory or the like) that may access a first image captured from a first vantage point by a first camera and a second image captured from a second vantage point by a second camera. The first and second cameras may both be included within a stereoscopic endoscope located at (e.g., extending into so as to be at least partially disposed within) a surgical area associated with a patient. For example, the surgical area may be fully or partially within the patient's body at a location where a surgical procedure is to be performed, is being performed, or has been performed. Additionally, the first and second vantage points of the first and second cameras may be stereoscopic to one another. In other words, the vantage points may be disposed relatively near to one another in space (e.g., at left and right sides of a distal tip of the stereoscopic endoscope) and may be aligned so as to point toward a same target area.

The measurement system may receive user input designating a user-selected two-dimensional ("2D") endpoint corresponding to a feature within the surgical area. The user input may be provided, for example, by the user selecting (e.g., touching, clicking on, etc.) a point within the first image that corresponds to a location of the feature within the first image. Based on the user-selected 2D endpoint, the measurement system may identify a matched 2D endpoint corresponding to the feature as represented in the second image. Subsequently, based on the user-selected and matched 2D endpoints, the measurement system may define a three-dimensional ("3D") endpoint corresponding to the feature within the surgical area. For example, while the user-selected and matched 2D endpoints may constitute different pixels or pixel groups within the first and second images, the 3D endpoint may constitute 3D coordinates defining a particular point in space with respect to a particular coordinate system (e.g., a coordinate system associated with the surgical area, with the stereoscopic endoscope, with a robotic surgical system associated with the measurement system, or the like).

Once a 3D endpoint has been defined in this way, the measurement system may determine a distance from the 3D endpoint to an additional 3D endpoint corresponding to an additional feature within the surgical area. In some examples, the additional 3D endpoint may be a user-selected 3D endpoint defined based on a user-selected 2D endpoint in a similar manner as described above. In other examples, the additional 3D endpoint may be a non-user-selected 3D endpoint. For instance, the additional 3D endpoint may correspond to a location of a particular surgical instrument, to a location of the stereoscopic endoscope, to an origin point defined within the surgical area or the coordinate system, or to any other location within the surgical area as may serve a particular implementation. Various manners in which the measurement system may determine a distance between 3D endpoints will be described herein.

Various benefits may be provided by the systems and methods disclosed herein. For example, the systems and methods disclosed herein may facilitate point-to-point measurements of anatomical features or other points of interest within a patient's body during a minimally invasive surgical procedure at least as conveniently and accurately as might be possible in an open surgical procedure in which such features are openly accessible. For example, the systems and methods disclosed herein may facilitate measurement of a size of a hernia so that a mesh patch may be cut to an appropriate size to properly patch the hernia, a size of a mitral valve for a mitral valve repair operation, a size of a tumor to determine how much energy may be required to properly eradicate the tumor, and/or a size of any other anatomical feature within a patient. Additionally or alternatively, the systems and methods disclosed herein may facilitate measurement of a distance between a tip of a surgical instrument and tissue within the patient, a distance between two different surgical instruments disposed within a surgical area of a patient, and/or any other distance within the patient that may be useful for a surgical team to know during a minimally invasive surgical procedure. Accordingly, the systems and methods described herein may help make minimally invasive surgical procedures increasingly safe, effective, and attractive to patients and surgeons.

Moreover, the systems and methods disclosed herein may be relatively more accurate, more effective, and/or easier to use than conventional techniques used to measure distances within surgical areas associated with minimally invasive surgical procedures. For example, the systems and methods disclosed herein do not require a user to designate 3D endpoints for a measurement by manually positioning surgical instrument tips at particular 3D endpoints, as the user would have to do using conventional techniques that rely exclusively on kinematic data to estimate distances within surgical areas. As another example, the systems and methods described herein may facilitate relatively easy and accurate measurement of a distance along a contour of an anatomical structure, which has heretofore been difficult or impossible in minimally invasive surgical procedures. Additionally, by allowing endpoints to be selected based only on 2D visuals, the systems and methods described herein may enable a team member other than a surgeon (e.g., a nurse, an assistant, etc.) to designate endpoints using screens that do not provide a stereoscopic 3D view, thereby freeing up the surgeon for other tasks to which the surgeon is uniquely suited.

The systems and methods disclosed herein may also advantageously utilize a minimal amount of computer processing resources, which may be beneficial in legacy systems that employ relatively outdated technology and that have relatively limited computer processing resources. For instance, many robotic surgical systems currently deployed may utilize relatively old computer hardware that was not designed to effectively perform large amounts of image processing (e.g., generating an entire 3D depth map from every point within stereoscopic images captured by a stereoscopic endoscope). Because the systems and methods do not require generating an entire 3D depth map in order to measure a point-to-point distance, such legacy robotic surgical systems may implement the systems and methods described herein.

Various embodiments will now be described in more detail with reference to the figures. The systems and methods described herein may provide one or more of the benefits mentioned above and/or various additional and/or alternative benefits that will be made apparent herein.

The systems and methods described herein may operate as part of or in conjunction with a robotic surgical system. As such, in order to promote an understanding of systems and methods described herein for measuring a distance using a stereoscopic endoscope, an exemplary robotic surgical system will now be described.

FIG. 1 illustrates an exemplary robotic surgical system 100. As shown, robotic surgical system 100 may include a patient-side system 102 (sometimes referred to as a patient-side cart), a surgeon console 104, and a vision cart 106 communicatively coupled one to another. Robotic surgical system 100 may be utilized by a surgical team to perform a robotically-enabled surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation. While FIG. 1 illustrates an ongoing minimally invasive surgical procedure, it will be understood that robotic surgical system 100 may similarly be used to perform open surgical procedures or other types of surgical procedures that may similarly benefit from the accuracy and convenience of robotic surgical system 100. Additionally, it will be understood that the surgical session throughout which robotic surgical system 100 may be employed may not only include an operative phase of a surgical procedure such as illustrated in FIG. 1, but may also include preoperative, postoperative, and/or other suitable phases of the surgical procedure.

As shown, patient-side system 102 may include a plurality of robotic arms 112 (e.g., robotic arms 112-1 through 112-4) to which a plurality of robotically-manipulated surgical instruments 114 (e.g., surgical instruments 114-1 through 114-4) may be coupled. Each surgical instrument 114 may be implemented by any suitable surgical tool, medical tool, monitoring instrument (e.g., an endoscope), diagnostic instrument, or the like that may be used for a robotically-enabled surgical procedure on patient 108 (e.g., by being at least partially inserted into patient 108 and manipulated to perform a robotically-enabled surgical procedure on patient 108). Note that while patient-side system 102 is depicted and described herein as a cart with a plurality of robotic arms 112 for exemplary purposes, in various other embodiments patient-side system 102 can include one or more carts, each with one or more robotic arms 112, one or more robotic arms 112 mounted on a separate structure within the operating room such as the operating table or the ceiling, and/or any other support structure(s). Patient-side system 102 will be described in more detail below.

Surgical instruments 114 may each be positioned at a surgical area associated with a patient. As used herein, a "surgical area" associated with a patient may, in certain examples, be entirely disposed within the patient and may include an area within the patient near where a surgical procedure is planned to be performed, is being performed, or has been performed. For example, for a minimally invasive surgical procedure being performed on tissue internal to a patient, the surgical area may include the tissue as well as space around the tissue where, for example, surgical instruments being used to perform the surgical procedure are located. In other examples, a surgical area may be at least partially disposed external to the patient. For instance, robotic surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument (e.g., any of surgical instruments 114) may be referred to as being "located at" (or "located within") a surgical area when at least a portion of the surgical instrument is disposed within the surgical area.

Surgeon console 104 may be configured to facilitate control by surgeon 110-1 of robotic arms 112 and surgical instruments 114. For example, surgeon console 104 may provide surgeon 110-1 with imagery (e.g., high-definition 3D imagery) of a surgical area associated with patient 108 as captured by an endoscope. Surgeon 110-1 may utilize the imagery to perform one or more procedures with surgical instruments 114.

To facilitate control of surgical instruments 114, surgeon console 104 may include a set of master controls 116 (shown in close-up view 118). Master controls 116 may be manipulated by surgeon 110-1 in order to control movement of surgical instruments 114. Master controls 116 may be configured to detect a wide variety of hand, wrist, and finger movements by surgeon 110-1. In this manner, surgeon 110-1 may intuitively perform a procedure using one or more of surgical instruments 114. For example, as depicted in close-up view 120, functional tips of surgical instruments 114-1 and 114-4 coupled to robotic arms 112-1 and 112-4, respectively, may mimic the dexterity of the hand, wrist, and fingers of surgeon 110-1 across multiple degrees of freedom of motion in order to perform one or more surgical procedures (e.g., an incision procedure, a suturing procedure, etc.).

Although surgeon console 104 is depicted and described herein as a single unit for exemplary purposes, in various other embodiments surgeon console 104 can include a variety of discrete components, such as wired or wireless master controls 116, a separate display element(s) (e.g., a projector or head-mounted display), separate data/communications processing hardware/software, and/or any other structural or functional elements of surgeon console 104. Surgeon console 104 will be described in more detail below.

Vision cart 106 may be configured to present visual content to surgical team members 110 who may not have access to the images provided to surgeon 110-1 at surgeon console 104. To this end, vision cart 106 may include a display monitor 122 configured to display one or more user interfaces, such as images (e.g., 2D images) of the surgical area, information associated with patient 108 and/or the surgical procedure, and/or any other visual content as may serve a particular implementation. For example, display monitor 122 may display images of the surgical area together with additional content (e.g., graphical content, contextual information, etc.) overlaid on top of or otherwise concurrently displayed with the images. In some embodiments, display monitor 122 is implemented by a touchscreen display with which surgical team members 110 may interact (e.g., by way of touch gestures) to provide user input to robotic surgical system 100.

Patient-side system 102, surgeon console 104, and vision cart 106 may be communicatively coupled one to another in any suitable manner. For example, as shown in FIG. 1, patient-side system 102, surgeon console 104, and vision cart 106 may be communicatively coupled by way of control lines 124, which may represent any wired or wireless communication link as may serve a particular implementation. To this end, patient-side system 102, surgeon console 104, and vision cart 106 may each include one or more wired or wireless communication interfaces, such as one or more local area network interfaces, Wi-Fi network interfaces, cellular interfaces, etc.

Patient-side system 102, surgeon console 104, and vision cart 106 may each include at least one computing device configured to control, direct, and/or facilitate operations of robotic surgical system 100. For example, surgeon console 104 may include a computing device configured to transmit instructions by way one or more of control lines 124 to patient-side system 102 in order to control movement of robotic arms 112 and/or surgical instruments 114 in accordance with manipulation by surgeon 110-1 of master controls 116. In some examples, vision cart 106 may include one or more computing devices configured to perform primary processing operations of robotic surgical system 100. In such configurations, the one or more computing devices included in vision cart 106 may control and/or coordinate operations performed by various other components (e.g., by patient-side system 102 and/or surgeon console 104) of robotic surgical system 100. For example, a computing device included in surgeon console 104 may transmit instructions to patient-side system 102 by way of the one or more computing devices included in vision cart 106.

Figure 2:
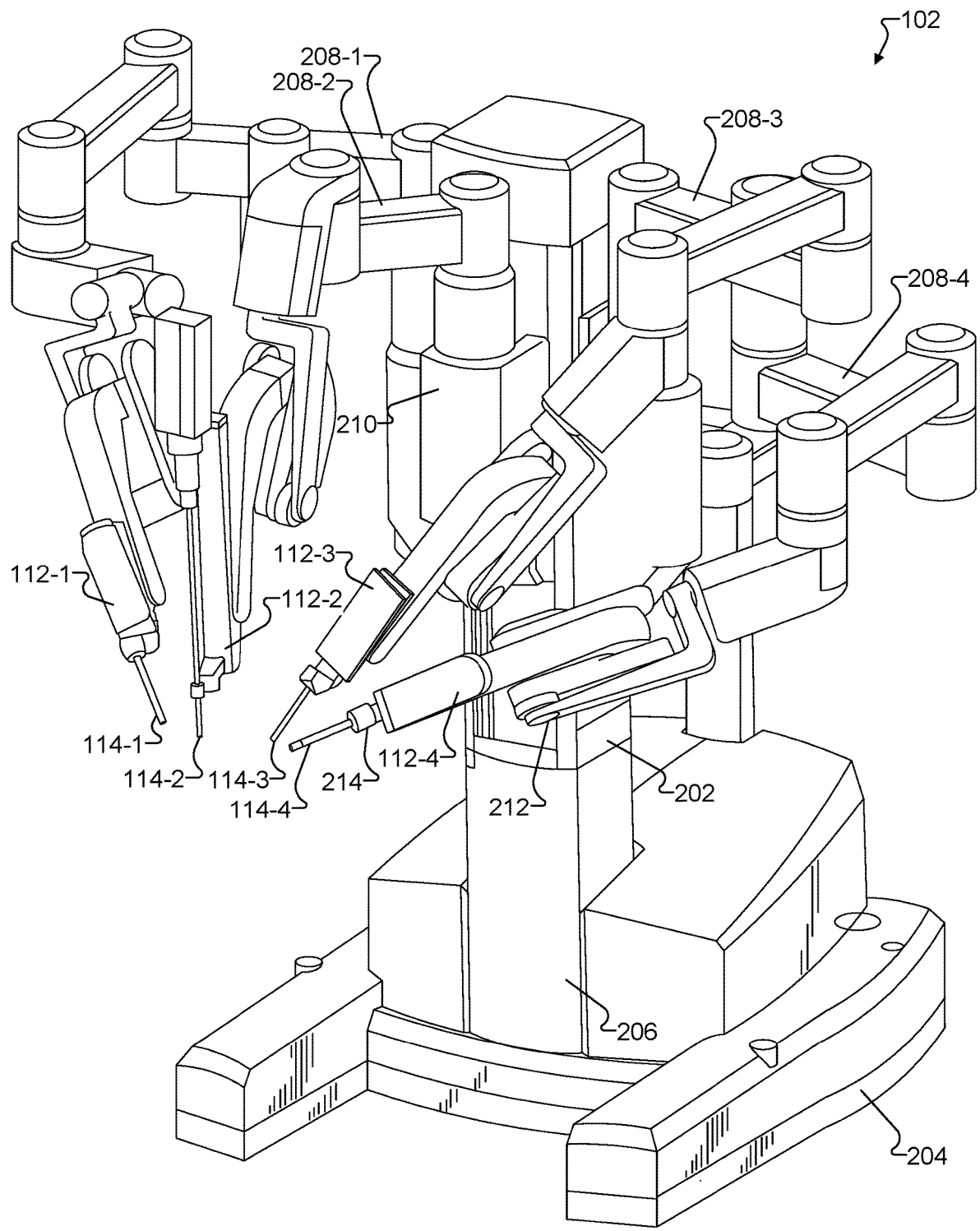
FIG. 2 illustrates an exemplary patient-side system included within the robotic surgical system of FIG. 1 according to principles described herein.

FIG. 2 illustrates a perspective view of patient-side system 102. As shown, patient-side system 102 includes a cart column 202 supported by a base 204. In some examples, cart column 202 may include a protective cover 206 that protects components of a counterbalance subsystem and a braking subsystem disposed within cart column 202 from contaminants.

Cart column 202 may support a plurality of setup arms 208 (e.g., setup arms 208-1 through 208-4) mounted thereon. Each setup arm 208 may include a plurality of links and joints that allow manual positioning of setup arms 208, and may each be connected to one of robotic arms 112. In the example of FIG. 2, patient-side system 102 includes four setup arms 208 and four robotic arms 112. However, it will be recognized that patient-side system 102 may include any other number of setup arms 208 and robotic arms 112 as may serve a particular implementation.

Setup arms 208 may be non-robotically controllable and configured to statically hold each robotic arm 112 in a respective position desired by a person setting up or reconfiguring patient-side system 102. Setup arms 208 may be coupled to a carriage housing 210 and manually moved and situated during a preoperative, operative, or postoperative phase of a surgical session. For example, setup arms 208 may be moved and situated during a preoperative phase when robotic surgical system 100 is being prepared and/or targeted for a surgical procedure to be performed. In contrast, robotic arms 112 may be robotically controlled (e.g., in response to manipulation of master controls 116, as described above).

As shown, each robotic arm 112 may have a surgical instrument 114 coupled thereto. In certain examples, three of the four robotic arms 112 may be configured to move and/or position surgical instruments 114 that are used to manipulate patient tissue and/or other objects (e.g., suturing materials, patching materials, etc.) within the surgical area. Specifically, as shown, robotic arms 112-1, 112-3, and 112-4 may be used, respectively, to move and/or position surgical instruments 114-1, 114-3, and 114-4. A fourth robotic arm 112 (e.g., robotic arm 112-2 in the example of FIG. 2) may be used to move and/or position a monitoring instrument (e.g., a stereoscopic endoscope), as will be described in more detail below.

Robotic arms 112 may each include one or more displacement transducers, orientational sensors, and/or positional sensors (e.g., sensor 212) used to generate raw (i.e., uncorrected) kinematics information to assist in control and tracking of surgical instruments 114. For example, kinematics information generated by the transducers and the sensors in patient-side system 102 may be transmitted to an instrument tracking system of robotic surgical system 100 (e.g., a computing device included in vision cart 106). Each surgical instrument 114 may similarly include a displacement transducer, a positional sensor, and/or an orientation sensor (e.g., sensor 214) in certain implementations, each of which may provide additional kinematics information to the tracking system. The tracking system may process the kinematics information received from the sensors included on robotic arms 112 and/or surgical instruments 114 to perform various operations, such as determining current positions of robotic arms 112 and/or surgical instruments 114. Additionally, one or more surgical instruments 114 may include a marker (not explicitly shown) to assist in acquisition and tracking of surgical instruments 114 as may serve a particular implementation.

Figure 3:
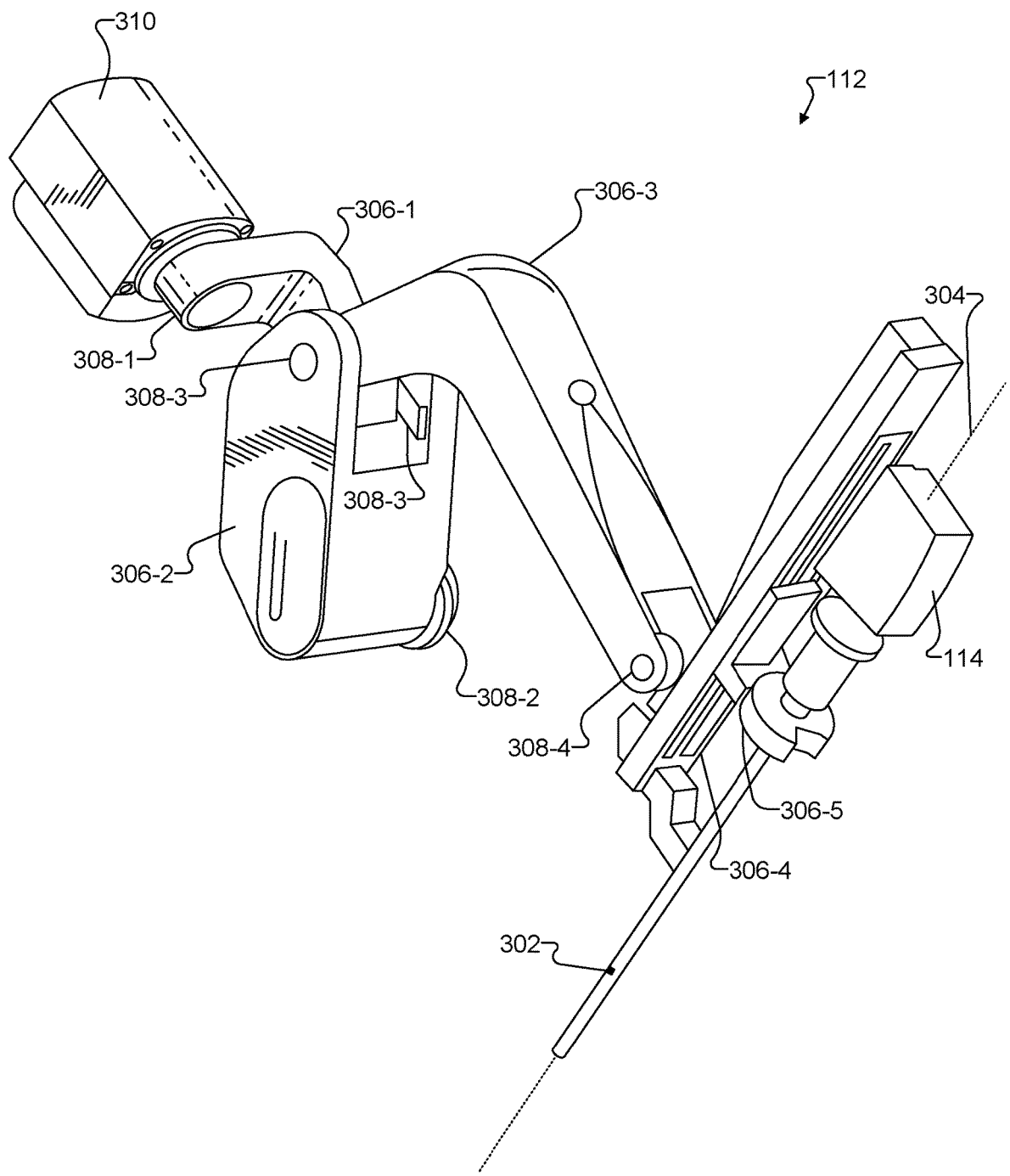
FIG. 3 illustrates an exemplary robotic arm included within the patient-side system of FIG. 2 according to principles described herein.

FIG. 3 illustrates a perspective view of an exemplary robotic arm 112 (e.g., any one of robotic arms 112-1 through 112-4). As shown, a surgical instrument 114 may be removably coupled to robotic arm 112. In the example of FIG. 3, surgical instrument 114 is an endoscopic device (e.g., a stereo laparoscope, an arthroscope, a hysteroscope, or another type of stereoscopic or monoscopic endoscope). Alternatively, surgical instrument 114 may be a different type of imaging device (e.g., an ultrasound device, a fluoroscopy device, an MRI device, etc.), a grasping instrument (e.g., forceps), a needle driver (e.g., a device used for suturing), an energy instrument (e.g., a cautery instrument, a laser instrument, etc.), a retractor, a clip applier, a probe grasper, a cardiac stabilizer, or any other suitable instrument or tool.

In some examples, it may be desirable for robotic arm 112 and surgical instrument 114 coupled to robotic arm 112 to move around a single fixed center point 302 so as to constrain movement of center point 302. For example, center point 302 may be located at or near a point of insertion of a surgical instrument 114 into patient 108. In certain surgical sessions (e.g., a surgical session associated with a laparoscopic surgical procedure), for instance, center point 302 may be aligned with an incision point to the internal surgical site by a trocar or cannula at an abdominal wall. As shown, center point 302 may be located on an insertion axis 304 associated with surgical instrument 114.

Robotic arm 112 may include a plurality of links 306 (e.g., links 306-1 through 306-5) pivotally coupled in series at a plurality of joints 308 (e.g., joints 308-1 through 308-4) near respective ends of links 306. For example, as shown, link 306-1 is pivotally coupled to a drive mount 310 at joint 308-1 near a first end of link 306-1, while being pivotally coupled to link 306-2 at joint 308-2 near a second end of link 306-1. Link 306-3 is pivotally coupled to link 306-2 near a first end of link 306-3 while being pivotally coupled to link 306-4 at joint 308-4 near a second end of link 306-3. Generally, link 306-4 may be substantially parallel to insertion axis 304 of surgical instrument 114, as shown. Link 306-5 is slidably coupled to link 306-4 to allow surgical instrument 114 to mount to and slide along link 306-5 as shown.

Robotic arm 112 may be configured to mount to a setup arm 208 (or a joint connected thereto) by way of drive mount 310 so as to be supported and held in place by setup arm 208, as described above. Drive mount 310 may be pivotally coupled to link 306-1 and may include a first internal motor (not explicitly shown) configured to yaw robotic arm 112 about a yaw axis of center point 302. In like manner, link 306-2 may house a second internal motor (not explicitly shown) configured to drive and pitch the linkage of robotic arm 112 about a pitch axis of center point 302. Likewise, link 306-4 may include a third internal motor (not explicitly shown) configured to slide link 306-5 and surgical instrument 114 along insertion axis 304. Robotic arm 112 may include a drive train system driven by one or more of these motors in order to control the pivoting of links 306 about joints 308 in any manner as may serve a particular implementation. As such, if surgical instrument 114 is to be mechanically moved, one or more of the motors coupled to the drive train may be energized to move links 306 of robotic arm 112.

Figure 4:
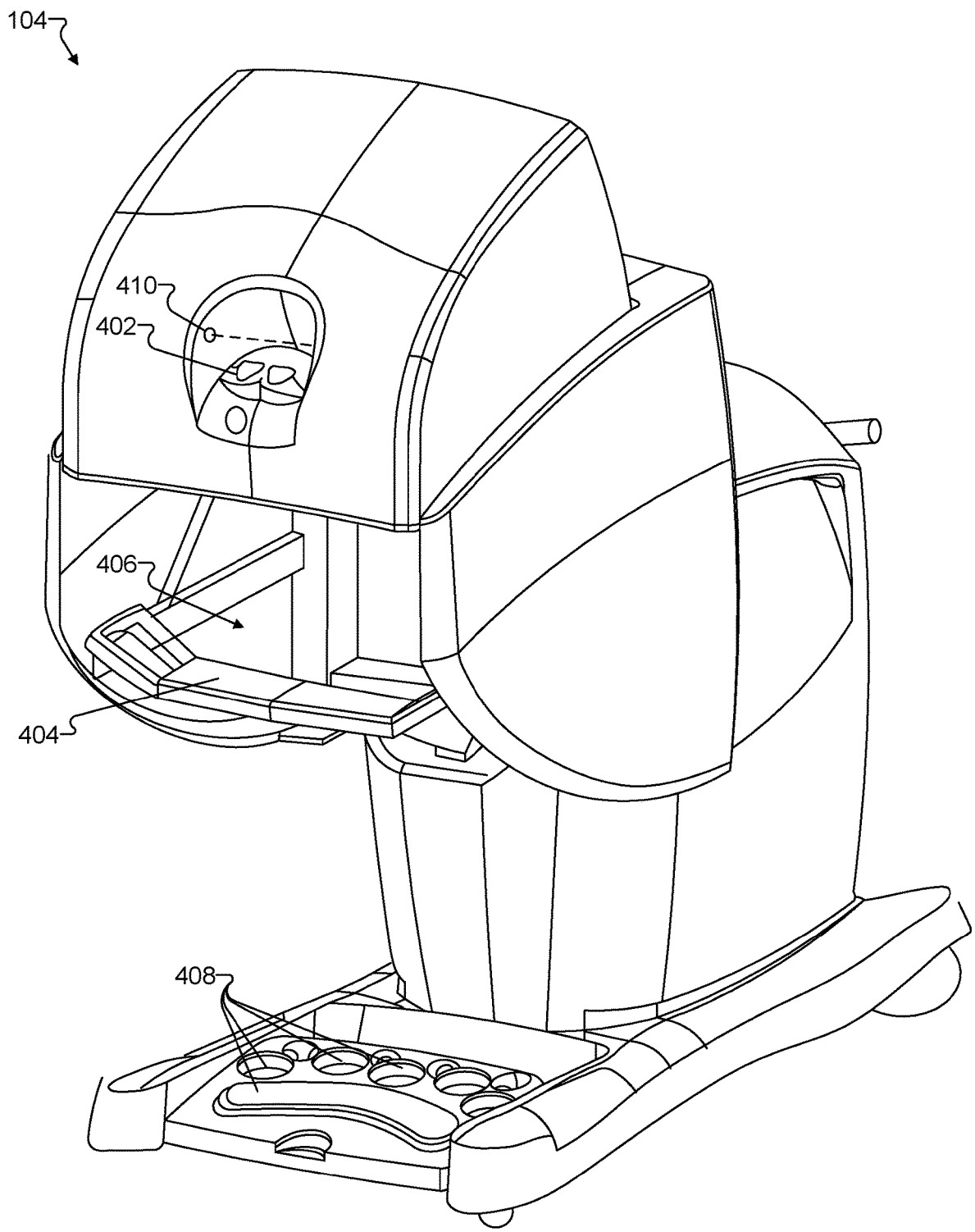
FIG. 4 illustrates an exemplary surgeon console included within the robotic surgical system of FIG. 1 according to principles described herein.

FIG. 4 illustrates a perspective view of surgeon console 104. As shown, surgeon console 104 may include a stereo viewer 402, an arm support 404, a controller workspace 406 within which master controls 116 (not shown in FIG. 4) are disposed, foot pedals 408, and a head sensor 410.

In some examples, stereo viewer 402 has two displays where stereoscopic 3D images of a surgical area associated with patient 108 and generated by a stereoscopic endoscope may be viewed by an operator (e.g., surgeon 110-1) during a surgical session. When using surgeon console 104, the operator may move his or her head into alignment with stereo viewer 402 to view the 3D images of the surgical area. To ensure that the operator is viewing the surgical area when controlling surgical instruments 114 of patient-side system 102, surgeon console 104 may use head sensor 410 disposed adjacent stereo viewer 402. Specifically, when the operator aligns his or her eyes with the binocular eye pieces of stereo viewer 402 to view a stereoscopic image of the surgical area, the operator's head may activate head sensor 410, which enables control of surgical instruments 114 by way of master controls 116. When the operator's head is removed from the area of stereo viewer 402, head sensor 410 may be automatically deactivated, which may prevent control of surgical instruments 114 by way of master controls 116. In this way, the position of surgical instruments 114 may remain static when robotic surgical system 100 detects that an operator is not actively engaged in attempting to control surgical instruments 114.

Arm support 404 may be used to support the elbows and/or forearms of the operator while he or she manipulates master controls 116 in order to control robotic arms 112 and/or surgical instruments 114. Additionally, the operator may use his or her feet to control foot pedals 408. Foot pedals 408 may be configured to change the configuration or operating mode of robotic surgical system 100, to generate additional control signals used to control surgical instruments 114, to facilitate switching control from one surgical instrument 114 to another, or to perform any other suitable operation.

Figure 5:
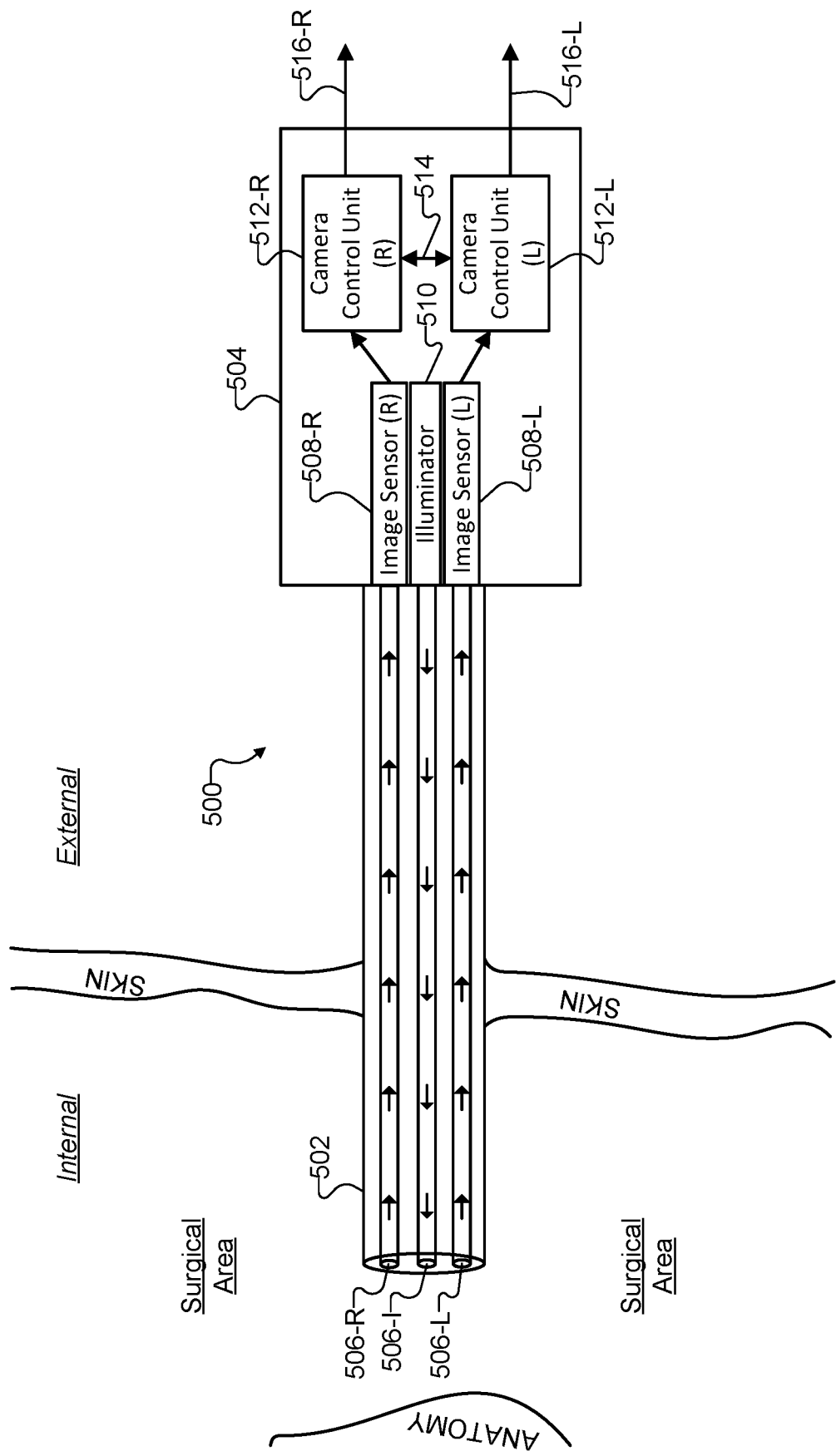
FIG. 5 illustrates an exemplary stereoscopic endoscope located at an exemplary surgical area associated with a patient according to principles described herein.

FIG. 5 illustrates an exemplary stereoscopic endoscope 500 included within robotic surgical system 100 and located at an exemplary surgical area associated with a patient. Stereoscopic endoscope 500 may be any one of surgical instruments 114 described above.

As shown, stereoscopic endoscope 500 may include a tube 502 having a distal tip that is configured to be inserted into a patient and a camera head 504 configured to be located external to the patient. Tube 502 may be coupled at a proximal end to camera head 504 and may be rigid (as shown in FIG. 5), jointed, and/or flexible as may serve a particular implementation.

Tube 502 may include a plurality of channels 506 (e.g., a right-side imaging channel 506-R, a left-side imaging channel 506-L, and an illumination channel 506-I) configured to conduct light between the surgical area internal to the patient and camera head 504. Each channel 506 may include one or more optical fibers configured to carry light along tube 502 such that light generated within camera head 504 may be carried by illumination channel 506-I to be output at a distal end of tube 502 and, after reflecting from patient anatomy and/or other objects within the surgical area, carried by imaging channels 506-R and 506-L from the distal end of tube 502 back to camera head 504. Arrows shown within channels 506 in FIG. 5 are depicted to indicate the direction that light may travel within each channel. Additionally, it will be understood that tube 502 may be associated with (e.g., include) one or more lenses or other suitable optics (not explicitly shown) for focusing, diffusing, or otherwise treating light carried by channels 506 as may serve a particular implementation. In various other embodiments, there may be additional imaging and/or illumination channels. In still other embodiments, one or more image sensors and/or illuminators can be positioned closer to the distal end of tube 502, thereby minimizing or even eliminating the need for imaging and/or illumination channels through tube 502.

In some examples, stereoscopic endoscope 500 may be coupled to a robotic arm of a robotic surgical system (e.g., one of robotic arms 112 of robotic surgical system 100) and positioned such that a distal tip of tube 502 is disposed within a surgical area of a patient. In this configuration, stereoscopic endoscope 500 may be referred to as being located at or within the surgical area, even though a portion of stereoscopic endoscope 500 (e.g., camera head 504 and a proximal portion of tube 502) may be located outside the surgical area. While stereoscopic endoscope 500 is located at the surgical area, light reflected from the surgical area may be captured by the distal tip of tube 502 and carried to camera head 504 by way of imaging channels 506-R and 506-L.

Camera head 504 may include various components configured to facilitate operation of stereoscopic endoscope 500. For example, as shown, camera head 504 may include image sensors 508 (e.g., an image sensor 508-R associated with right-side imaging channel 506-R and an image sensor 508-L associated with left-side imaging channel 506-L). Image sensors 508 may be implemented as any suitable image sensors such as charge coupled device ("CCD") image sensors, complementary metal-oxide semiconductor ("CMOS") image sensors, or the like. Additionally, one or more lenses or other optics may be associated with image sensors 508 (not explicitly shown). Camera head 504 may further include an illuminator 510 configured to generate light to travel from camera head 504 to the surgical area via illumination channel 506-I so as to illuminate the surgical area.

Camera head 504 may further include camera control units 512 disposed therein. Specifically, a camera control unit 512-R may be communicatively coupled to image sensor 508-R, and a camera control unit 512-L may be communicatively coupled to image sensor 508-L. Camera control units 512 may be synchronously coupled to one another by way of a communicative link 514, and may be implemented by software and/or hardware configured to control image sensors 508 so as to generate respective images 516 (i.e., an image 516-R associated with the right side and an image 516-L associated with the left side) based on light sensed by image sensors 508. As such, each respective combination of an imaging channel 506, an image sensor 508, a camera control unit 512, and associated optics may collectively be referred to as a camera included within stereoscopic endoscope 500. For example, stereoscopic endoscope 500 may include two such cameras, one for the left side and one for the right side. Such a camera may be said to capture an image 516 from a vantage point at a distal end of its respective imaging channel 506. Upon being generated by stereoscopic endoscope 500, images 516 may be accessed by a measurement system and/or otherwise used in any of the ways described herein. For example, images 516 may be used by a measurement system to measure a distance within a surgical area of a patient.

Figure 6:
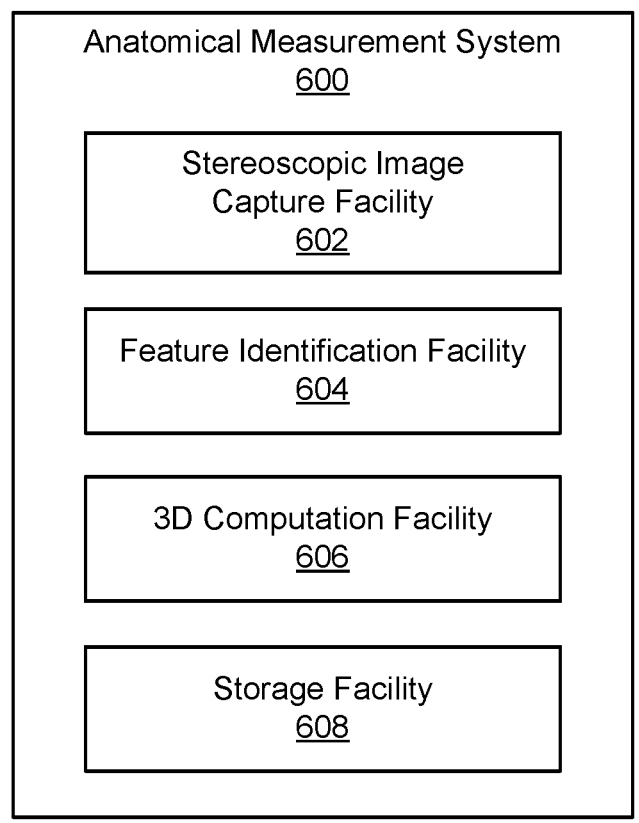
FIG. 6 illustrates an exemplary measurement system according to principles described herein.

To illustrate, FIG. 6 shows an exemplary measurement system 600 ("system 600") configured to measure a distance using images generated by a stereoscopic endoscope. As shown, system 600 may include, without limitation, a stereoscopic image capture facility 602, a feature identification facility 604, a 3D computation facility 606, and a storage facility 608 selectively and communicatively coupled to one another. It will be recognized that although facilities 602 through 608 are shown to be separate facilities in FIG. 6, facilities 602 through 608 may be combined into fewer facilities, such as into a single facility, or divided into more facilities as may serve a particular implementation. Each of facilities 602 through 608 may be implemented by any suitable combination of hardware and/or software.

System 600 may be associated with robotic surgical system 100 in any suitable manner. For example, system 600 may be implemented by or included within robotic surgical system 100. To illustrate, system 600 may be implemented by one or more computing devices included within patient-side system 102, surgeon console 104, and/or vision cart 106. System 600 may be additionally or alternatively implemented by stereoscopic endoscope 500, display monitor 122 of vision cart 106, stereo viewer 402 of surgeon console 104, one or more hardware components associated with a user interface (e.g., a touch screen, a computer mouse or other user input device, etc.), and/or any other components as may serve a particular implementation. In some examples, system 600 may be at least partially implemented by one or more computing devices communicatively coupled to, but not included in, robotic surgical system 100 (e.g., one or more servers communicatively coupled to robotic surgical system 100 by way of a network).

Stereoscopic image capture facility 602 may be configured to access images captured by a stereoscopic endoscope located at a surgical area associated with a patient. For example, in certain implementations, stereoscopic image capture facility 602 may access a first image (e.g., image 516-L) captured from a first vantage point by a first camera included within the stereoscopic endoscope located at the surgical area and a second image (e.g., image 516-R) captured from a second vantage point stereoscopic to the first vantage point by a second camera included within the stereoscopic endoscope.

Stereoscopic image capture facility 602 may access the images in any suitable manner. For example, stereoscopic image capture facility 602 may incorporate stereoscopic endoscope 500 and may access the images by capturing the images from respective stereoscopic vantage points (e.g., at the respective distal ends of imaging channels 506-L and 506-R) using the first and second cameras included within stereoscopic endoscope 500. In other implementations, stereoscopic image capture facility 602 may not incorporate stereoscopic endoscope 500 but may access images 516 by receiving them from stereoscopic endoscope 500.

Feature identification facility 604 may be configured to receive (e.g., from a user of system 600) user input designating a user-selected 2D endpoint corresponding to a feature within the surgical area as represented in the first image. Feature identification facility 604 may be further configured to identify, based on the user-selected 2D endpoint, a matched 2D endpoint corresponding to the feature as represented in the second image. Each of these operations will be described in more detail below.

As used herein, a "2D endpoint" may refer to a pixel or contiguous group of pixels that is included within a 2D image and that defines one endpoint of at least two endpoints between which a 3D measurement is to be made. For example, as used herein, a "user-selected 2D endpoint" may refer to a 2D endpoint that is manually selected by a user on a particular 2D image, while a corresponding "matched 2D endpoint" may refer to a 2D endpoint that is automatically identified as corresponding to the user-selected 2D endpoint on a different 2D image that is stereoscopic to the particular 2D image. Examples of user-selected 2D endpoints and corresponding matched 2D endpoints will be described and illustrated in more detail below.

3D computation facility 606 may be configured to define, based on the user-selected and matched 2D endpoints determined or identified by feature identification facility 604, a 3D endpoint corresponding to the feature within the surgical area to which the user-selected and matched 2D endpoints also correspond. 3D computation facility 606 may further be configured to determine a distance from the defined 3D endpoint to an additional 3D endpoint corresponding to an additional feature within the surgical area. The additional 3D endpoint may be derived based on an additional user-selected 2D endpoint, or may be determined or selected in another suitable manner as will be described in more detail below. Each of the operations performed by 3D computation facility 606 will be described in more detail below.

As used herein, a "3D endpoint" may refer to a point or position in 3D space with respect to a particular frame of reference such as a world coordinate system associated with system 600, stereoscopic endoscope 500, or the like. As described above, a 3D endpoint may be derived based on a 2D endpoint. However, unlike a 2D endpoint, which may only exist within the context of a particular image, a 3D endpoint may define three dimensions of a real point in space. As such, while a 2D endpoint may be associated with a particular 2D image, a 3D endpoint may be associated with anatomical or other features of real objects included in a surgical area represented by the particular 2D image.

Storage facility 608 may store and maintain any data received, generated, managed, maintained, used, and/or transmitted by facilities 602 through 606 in a particular implementation. For example, storage facility 608 may store program instructions (e.g., computer code) for performing operations described herein, image data, kinematic data, user input data, 3D location data, and/or any other data as may serve a particular implementation.

Various examples of distance measurement operations performed by system 600 will now be provided. It will be recognized that the examples provided herein are merely illustrative, and that system 600 may perform additional or alternative operations as may serve a particular implementation. It will also be recognized that system 600 may make measurements at any time during a surgical session. For example, while many exemplary measurements described herein are described as being performed intraoperatively (i.e., during the surgical procedure), various measurements may also be taken preoperatively (e.g., determining a tumor size to prepare to excise) or postoperatively (e.g., ensuring that a size of an excised crater from the tumor matches the expected preoperative size).

FIG. 7 illustrates exemplary images 702 (i.e., images 702-L and 702-R) of a surgical area associated with a patient as captured from stereoscopic vantage points by cameras included within stereoscopic endoscope 500. For example, images 702-L and 702-R may respectively implement images 516-L and 516-R described above. As shown, each image 702 depicts a representation of a hernia 704 that is to be measured so that, for example, a mesh patch may be cut to an appropriate size to properly patch the hernia 704.

As shown, images 702 are relatively similar one to another. However, it will be understood that slight differences also exist between images 702 due to the stereoscopic nature of the vantage points from which each image 702 is captured. As such, images 702 may appear to be three-dimensional when image 702-L is presented to a left eye of a user (e.g., surgeon 110-1) while image 702-R is presented to a right eye of the user.

As with images 516, either or both of images 702 may be displayed or presented by system 600 in any suitable way and/or on any suitable display screen. For instance, one or both of images 702 may be displayed on display monitor 122 of vision cart 106, on stereo viewer 402 on surgeon console 104, on a monoscopic display provided by stereoscopic endoscope 500, and/or on any other display screen associated with robotic surgical system 100 or system 600.

To measure a distance between features displayed in images 702 (e.g., a distance between edges of hernia 704), or between a feature displayed in images 702 and an additional feature not currently displayed in images 702, a user may interact with one or both of images 702 to designate one or more user-selected 2D endpoints that correspond to the feature(s).

Figure 8:
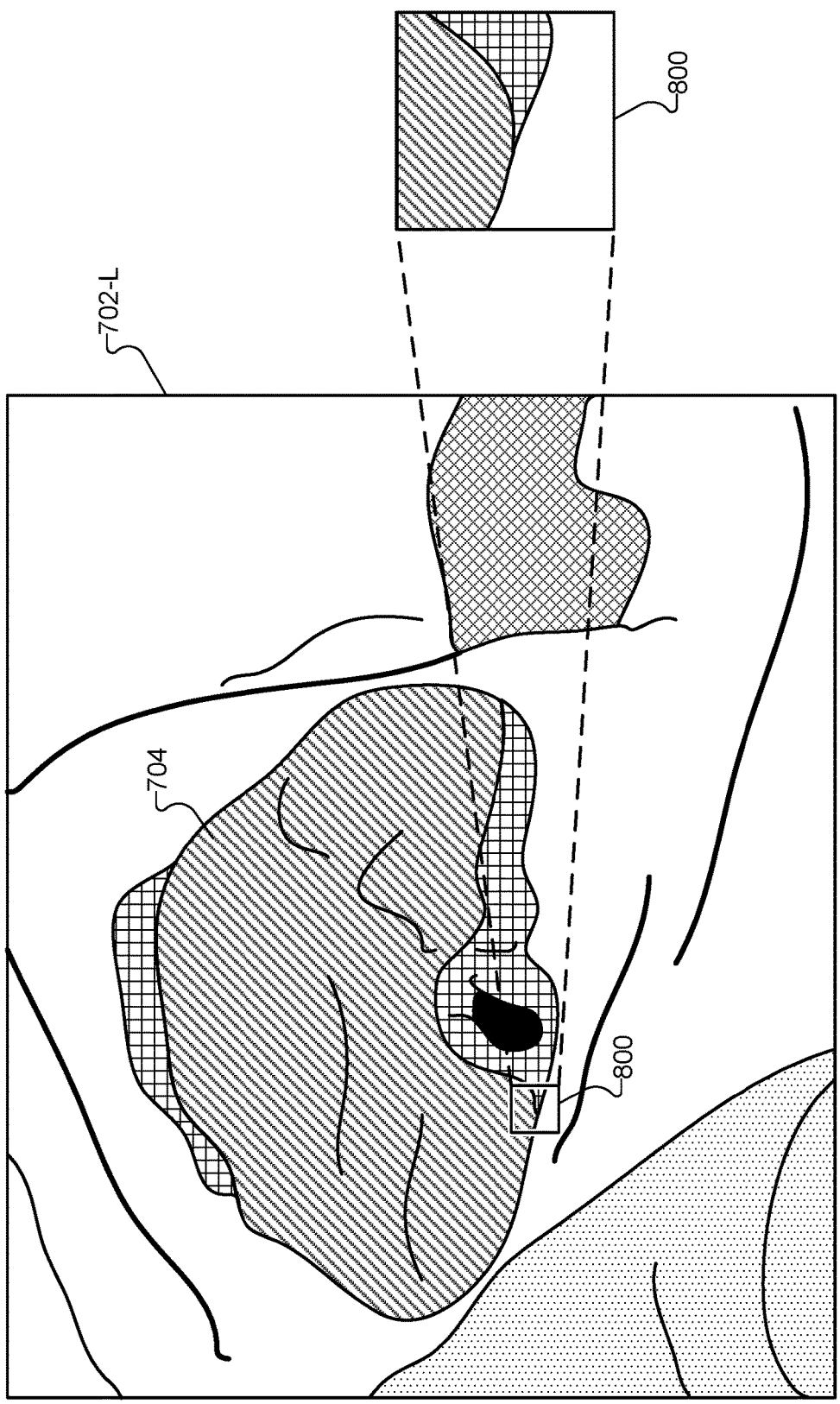
FIG. 8 illustrates an exemplary user-selected two-dimensional ("2D") endpoint designated by a user according to principles described herein.

To illustrate, FIG. 8 illustrates an exemplary user-selected 2D endpoint 800 designated by a user on image 702-L. While image 702-L is shown in FIG. 8, it will be recognized that the user-selected 2D endpoint 800 may alternatively be designated by the user on image 702-R. User-selected 2D endpoint 800 may correspond to a particular feature. As used herein, a "feature" to which an endpoint (e.g., a 2D or 3D endpoint) corresponds may refer to a particular component, point, or other feature of an anatomical structure or other object within a surgical area. For example, the feature to which user-selected 2D endpoint 800 corresponds is a particular part of an edge of hernia 704 (enlarged on the right-hand side of FIG. 8 to illustrate the feature in more detail). User-selected 2D endpoint 800 may include a plurality of pixels that collectively depict the corresponding feature in such a way that the feature may be identifiable when searched for within image 702-R as will be described in more detail below.

System 600 may receive any suitable type of user input designating user-selected 2D endpoint 800, and may facilitate the entering of such user input in various ways. For example, system 600 may receive the user input designating user-selected 2D endpoint 800 by providing image 702-L for display on a monoscopic display screen communicatively coupled with system 600, and receiving the user input as the user input is detected by a user interface associated with the display screen. For instance, system 600 may display image 702-L on display monitor 122 of vision cart 106, which may implement a touch screen configured to accept touch input from a user (e.g., any one of surgical team members 110). The user may provide the user input by touching a location on the touch screen that corresponds to the desired feature (e.g., an edge of hernia 704) displayed within image 702-L.

As another example of how user input designating user-selected 2D endpoint 800 may be received, system 600 may provide image 702-L for display on each display screen in a stereoscopic pair of display screens communicatively coupled with system 600, and may receive the user input as the user input is detected by a user interface associated with the stereoscopic pair of display screens. For instance, rather than directing image 702-L to be displayed on a left-side display screen of stereo viewer 402 of surgeon console 104 and image 702-R to be displayed on a right-side display screen of stereo viewer 402 of surgeon console 104 so as to provide a 3D view of the surgical area to a surgeon, system 600 may be configured, when requesting the user input designating user-selected 2D endpoint 800, to display the same image 702 (e.g., image 702-L in one example) on both sides of stereo viewer 402. In this way, system 600 may temporarily provide a 2D view of the surgical area to allow surgeon 110-1 to move a pointer object (e.g., a cursor) to a desired point on the duplicated image 702 and to thereby designate user-selected 2D endpoint 800.

User-selected 2D endpoint 800 may be designated by a surgeon using a stereo viewer in other suitable ways. As one example, for instance, one side of the stereo viewer may temporarily abstain from displaying an image 702 (e.g., image 702-R) while user-selected 2D endpoint 800 is designated using a pointer object presented on the other image 702 (e.g., image 702-L). As another example, both images 702-L and 702-R may be presented in the normal stereoscopic view (i.e., in 3D mode) and a pointer object may be made to appear to be floating above the tissue at a particular distance in front of the stereoscopic endoscope until user-selected 2D endpoint 800 is selected, at which point the cursor may appear to "fall" on to the tissue at a proper depth as a corresponding 3D endpoint is defined (as will be described below). Additionally, as yet another example, image 702-L and 702-R may be presented in the normal stereoscopic view and the user may select a point using a 3D cursor. A projection of this selected point onto one of the images (e.g., image 702-L) may then be used as user-selected 2D endpoint 800.

In some examples, a designation of a user-selected 2D endpoint (e.g., user-selected 2D endpoint 800) may be performed as a discrete event such as a touch gesture, a button press, a mouse click, a button release (e.g., to end a dragging motion from one user-selected 2D endpoint to another), or the like. For example, system 600 may receive the user input by providing image 702-L for display on a display screen communicatively coupled with system 600 (e.g., stereo viewer 402, display monitor 122, etc.), providing a user interface that is associated with the display screen and that includes a pointer object configured to be moved by the user to any point on the display screen, and receiving the user input designating the user-selected 2D endpoint as a discrete user selection of a particular point on the display screen to which the user has moved the pointer object.

In other examples, the user selection of the user-selected 2D endpoint may be performed dynamically as a pointer object (e.g., a cursor) is moved within a display screen without any additional user selection action (i.e., without an action such as a button press, mouse click, or the like). In other words, in certain implementations, many user-selected 2D endpoints for many different potential measurements may be automatically selected as a user moves the pointer object on the display. In this way, for example, the pointer object may be dynamically updated in both sides of stereo viewer 402 so as to appear to move along the surface of the tissue in 3D.

Once user-selected 2D endpoint 800 has been designated within one of images 702 (e.g., image 702-L) by a user in any of these or other suitable ways, system 600 may identify a matched 2D endpoint within the other image (e.g., image 702-R) that corresponds to the same feature to which user-selected 2D endpoint 800 corresponds (i.e., the same part of the edge of hernia 704 in this example).

Figure 9:
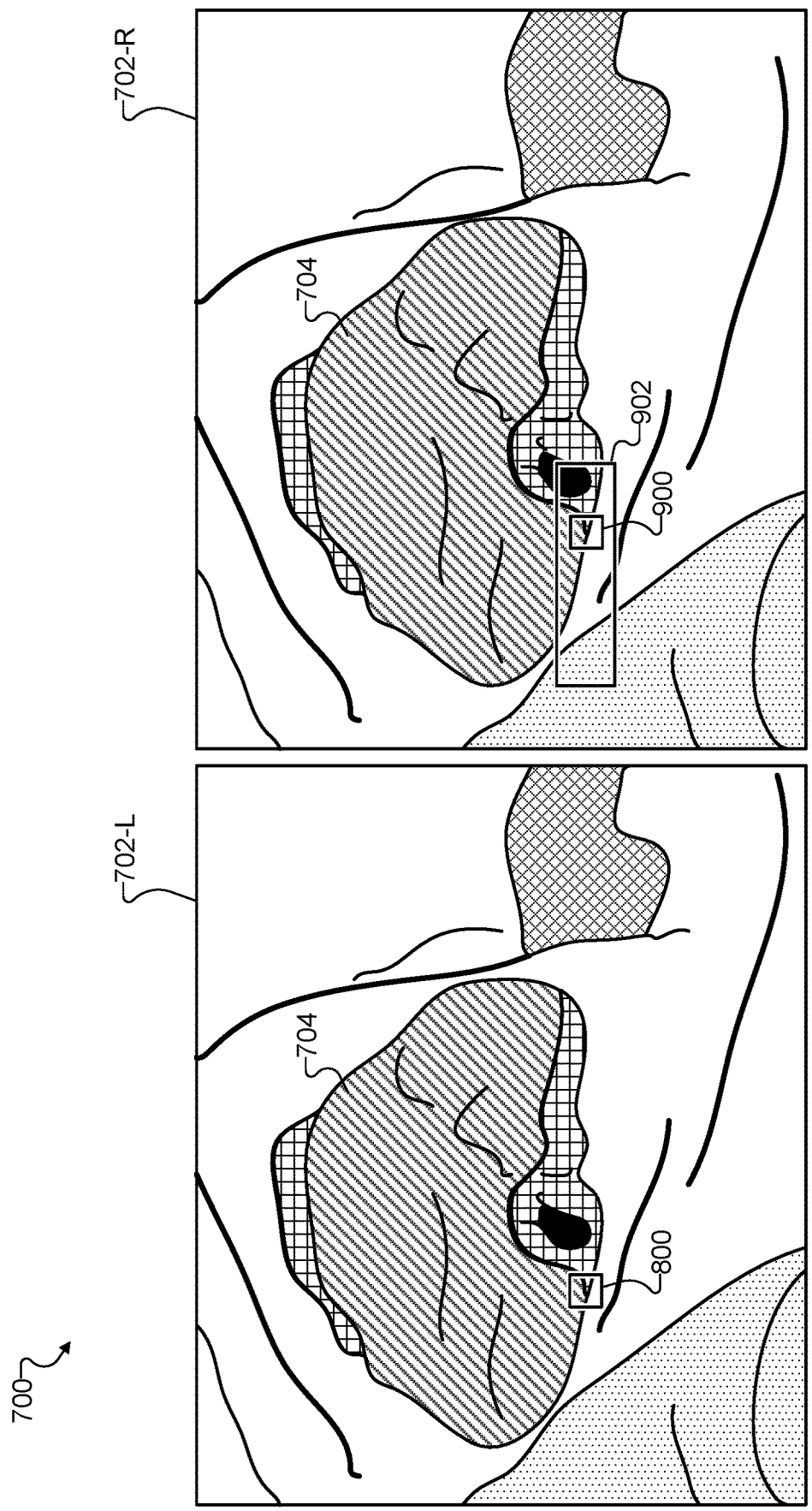
FIG. 9 illustrates an exemplary matched 2D endpoint identified to correspond to a same feature within the surgical area as the user-selected 2D endpoint illustrated in FIG. 8 according to principles described herein.

To illustrate, FIG. 9 depicts an exemplary matched 2D endpoint 900 that is to be identified as corresponding to a same feature within the surgical area as user-selected 2D endpoint 800. As described above, system 600 may identify matched 2D endpoint 900 based on user-selected 2D endpoint 800 in response to a discrete event such as a touch of a screen or a button press, or automatically (e.g., as a pointer object is moved around image 702-L) so as to provide an appearance of a 3D pointer object that moves along the tissue as described above.

In certain examples, the cameras of stereoscopic endoscope 500 may be calibrated to be perfectly rectified (i.e., to point in parallel directions). In such examples, matched 2D endpoint 900 may be located within a particular range of pixel columns on a particular pixel row within image 702-R (i.e., a pixel row corresponding to a pixel row of image 702-L upon which user-selected 2D endpoint 800 is located). In contrast, in other examples, the cameras of stereoscopic endoscope 500 may not be rectified, but may be configured, for example, to point slightly inward toward a target area at a nominal working depth (e.g., approximately 50 mm from the distal tip of stereoscopic endoscope 500). In these examples, matched 2D endpoint 900 may be located somewhere within a rectangular area 902 that spans a particular range of pixel columns and pixel rows within image 702-R.

Pixels included within the range of columns on the particular row or range of rows may define a plurality of candidate pixel blocks, one of which may be identified by system 600 as matched 2D endpoint 900 based on a strong match with user-selected 2D endpoint 800. More specifically, if user-selected 2D endpoint 800 is implemented as a pixel block including a first number of rows and a first number of columns, system 600 may identify matched 2D endpoint 900 in the following manner.

First, system 600 may identify rectangular area 902 (i.e., the area where a matched 2D endpoint for user-selected 2D endpoint 800 is expected to be) within image 702-R. Rectangular area 902 may be identified in any suitable manner. For example, system 600 may identify rectangular area 902 based on calibration of the stereoscopic endoscope (e.g., intrinsic parameters of the cameras, a target or actual alignment of the cameras, etc.), an approximation of how proximate stereoscopic endoscope 500 is to the tissue when images 702 are captured (e.g., determined based on kinematic or other data as will be described in more detail below), and/or any other suitable information as may serve a particular implementation.

As shown in FIG. 9, rectangular area 902 may be identified as a relatively wide, short area that includes a plurality of candidate pixel blocks that each include the first number of rows and the first number of columns. In some examples, rectangular area 902 may include a second number of rows greater than the first number of rows (such that rectangular area 902 is taller than user-selected 2D endpoint 800) and a second number of columns greater than the first number of columns (such that rectangular area 902 is wider than user-selected 2D endpoint 800). The second number of columns included in rectangular area 902 may be at least two times greater than the second number of rows such that rectangular area 902 has a short, wide shape as shown in FIG. 9.

Once rectangular area 902 is identified, system 600 may analyze candidate pixel blocks in the plurality of candidate pixel blocks included within rectangular area 902 to assign, to each analyzed candidate pixel block, a respective similarity metric with respect to user-selected 2D endpoint 800. Based on this analysis, system 600 may identify as matched 2D endpoint 900 a particular candidate pixel block that is assigned the highest similarity metric out of all of the similarity metrics assigned to the plurality of candidate pixel blocks.

Figure 10:
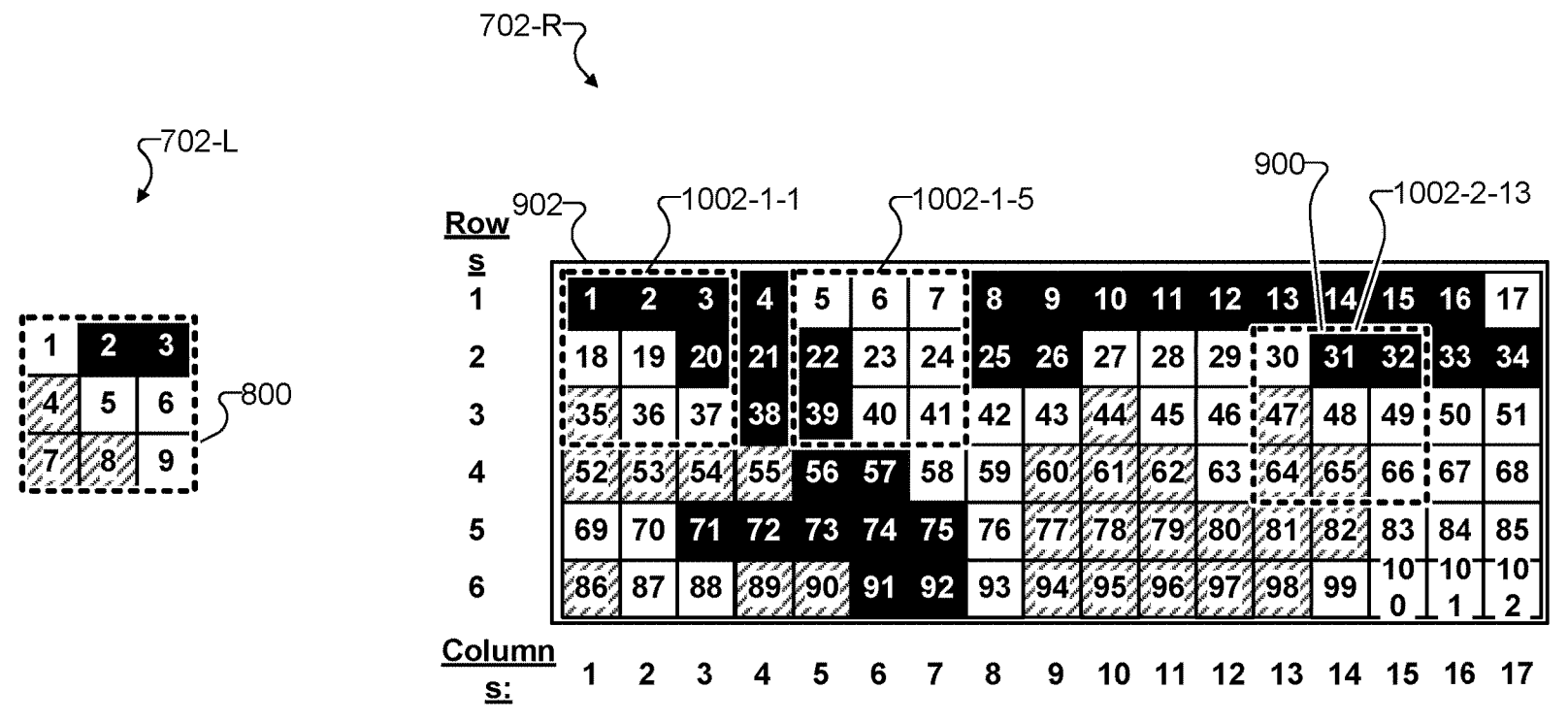

To illustrate, FIG. 10 depicts a zoomed in, pixel-level view of user-selected 2D endpoint 800 within image 702-L and matched 2D endpoint 900 within rectangular area 902 in image 702-R. Specifically, user-selected 2D endpoint 800 is illustrated as a 3×3 block of pixels labeled 1 through 9, while rectangular area 902 is illustrated as a 17×6 block of pixels labeled 1 through 102. In the description below, pixels included within image 702-L (i.e., pixels in user-selected 2D endpoint 800) will be referred to as pixels 1L, 2L, 3L, and so forth, while pixels included within image 702-R (i.e., pixels in rectangular area 902) will be referred to as pixels 1R, 2R, 3R, and so forth. Each pixel in FIG. 10 is depicted as being either white, black, or shaded to represent different color values, grayscale values, etc. with which the pixels may be associated. It will be understood, however, that the shading of the pixels in FIG. 10 is intended to aid in the description of FIG. 10 and, as such, may not align with the anatomy as depicted in images 702-L and 702-R.

As described above, system 600 may define rectangular area 902 within image 702-R so that matched 2D endpoint 900 is guaranteed to be contained somewhere within rectangular area 902. However, analysis may be required to determine exactly where within rectangular area 902 matched 2D endpoint 900 is located. For illustrative purposes, FIG. 10 shows matched 2D endpoint 900 (i.e., comprising pixels 30R-32R, 47R-49R, and 64R-66R) as a perfect match with user-selected 2D endpoint 800. However, it will be understood that, with real images that include complex details and color palettes, such a perfect match may be unlikely to be found. Rather, system 600 may be configured to analyze each candidate pixel block included within rectangular area 902 to identify a pixel block that is the closest match to user-selected 2D endpoint 800. To this end, system 600 may analyze a plurality of candidate pixels blocks 1002 (e.g., candidate pixel blocks 1002-1-1, 1002-1-5, 1002-2-13, and others not explicitly labeled).

Each candidate pixel block 1002 in rectangular area 902 may be referred to herein based on a row number and a column number of the top left pixel, as labeled along the sides of rectangular area 902. For example, the candidate pixel block 1002 in the top left corner of rectangular area 902 is referred to as candidate pixel block 1002-1-1 due to the position of its top left pixel (i.e. pixel 1R) at row 1 and column 1, the candidate pixel block labeled a few columns to the right of candidate pixel block 1002-1-1 is referred to as candidate pixel block 1002-1-5 due to the position of its top left pixel (i.e. pixel 5R) at row 1 and column 5, and so forth.

System 600 may analyze each candidate pixel block 1002 and assign each candidate pixel block 1002 a particular similarity metric based on how similar each candidate pixel block 1002 is to user-selected 2D endpoint 800. For example, system 600 may assign a similarity metric to each candidate pixel block included in rectangular area 902 by analyzing the candidate pixel blocks in a sequential, parallel, or other suitable manner. Such similarity metrics may be computed and assigned in accordance with any suitable pixel comparison technique. For instance, in one technique, system 600 may base a similarity metric on a sum of absolute differences (e.g., color value differences) between each pixel in the individual candidate pixel block and a corresponding pixel in user-selected 2D endpoint 800. For example, system 600 may compare candidate pixel block 1002-1-5 to user-selected 2D endpoint 800 by comparing pixels 1L and 5R to determine that they are the same (i.e., because they are both white), pixels 2L and 6R to determine that they are very different (i.e., because one is white while the other is black), pixels 4L and 22R to determine that they are somewhat different (i.e., because one is shaded and the other is black), and so forth. Based on an overall sum of the differences between all such corresponding pairs of pixels, system 600 may assign a relatively low similarity metric to candidate pixel block 1002-1-5 because user-selected 2D endpoint 800 and candidate pixel block 1002-1-5 are not particularly similar to one another (i.e., there is not a good match). However, when system 600 performs a similar analysis on candidate pixel block 1002-2-13 (i.e., comparing pixels 1L and 30R, 2L and 31R, etc.) system 600 may assign a relatively high similarity metric to candidate pixel block 1002-2-13 since there are no differences between candidate pixel block 1002-2-13 and user-selected 2D endpoint 800, thus constituting a good match. If this similarity metric is as high or higher than any other assigned similarity metric, system 600 may identify pixel block 1002-2-13 to be matched 2D endpoint 900 that corresponds to user-selected 2D endpoint 800. For this reason, candidate pixel block 1002-2-13 is also labeled as matched 2D endpoint 900.

Other techniques besides the sum of absolute differences described above may also be used in certain implementations. For instance, in some implementations, system 600 may base computed similarity metrics on a sum of squared differences between each pixel 1000-R in each individual candidate pixel block 1002 and each corresponding pixel 1000-L of the pixel block of user-selected 2D endpoint 800. In the same or other implementations, system 600 may base computed similarity metrics on a normalized cross correlation between each pixel 1000-R in each individual candidate pixel block 1002 and each corresponding pixel 1000-L of the pixel block of user-selected 2D endpoint 800. In still other examples, system 600 may compute similarity metrics based on data transformation techniques (e.g., census transforms, rank transforms, etc.), sift descriptors, gradients (i.e., sums of absolute differences between horizontal and vertical gradients), or any other techniques as may serve a particular implementation. Additionally, in some examples, a combination of two or more of the techniques described herein may be employed. For instance, system 600 may base computed similarity metrics on a sum of absolute differences and a census transform in one exemplary implementation.

Once a particular candidate pixel block 1002 such as candidate pixel block 1002-2-13 has been identified as being the best match to user-selected 2D endpoint 800, it may be desirable to determine an objective confidence level associated with the likelihood that this candidate pixel block is an accurate and unique match. This confidence level may then be used to help define (or to determine whether it will be worth defining) the 3D endpoint corresponding to the same feature. For example, if it is determined that the most likely match has a relatively low likelihood of being an accurate and unique match, it may be desirable for system 600 to abstain from determining a measurement based on the low-confidence endpoint and to indicate to the user that a measurement could not be performed based on the designated user-selected 2D endpoint and that the user must designate another user-selected 2D endpoint, or that a measurement based on the low-confidence endpoint is subject to a relatively high margin of error.

A match confidence level associated with a particular match (i.e., a particular candidate pixel block identified as being a matched 2D endpoint) may be determined in any suitable way. For instance, subsequent to the identification of matched 2D endpoint 900, system 600 may identify, based on matched 2D endpoint 900, a reverse-matched 2D endpoint corresponding to the same feature as represented in image 702-L. In other words, system 600 may perform the same process from image 702-R to image 702-L as described above (e.g., identifying a rectangular area, assigning similarity metrics for each candidate pixel block within the rectangular area, etc.) to identify a reverse-matched 2D endpoint (i.e., the best match for candidate pixel block 1002-2-13) within image 702-L. System 600 may thus determine a match confidence value for the matched 2D endpoint based on the user-selected and reverse-matched 2D endpoints. For example, if the reverse-matched 2D endpoint aligns with or is very close to user-selected 2D endpoint 800, the match confidence value may be relatively high, whereas if the reverse-matched 2D endpoint is not particularly nearby user-selected 2D endpoint 800, the match confidence value may be relatively low.

In addition to determining bilateral consistency between the user-selected 2D endpoint and the matched 2D endpoint in this way, other techniques may also be used to determine a confidence level. For example, consistency in the local neighborhood around a user-selected 2D endpoint and a matched 2D endpoint may further indicate a likelihood that the matched 2D endpoint was identified correctly. Specifically, a few points around a user-selected 2D endpoint and a matched 2D endpoint may be compared to ensure that disparity estimates are consistent between the points.

In some examples, a match confidence value may be calculated based on how much better of a match a first candidate pixel block identified as being the closest match to the user-selected 2D endpoint (the "best match") is than a second candidate pixel block identified as being the second-closest match to the user-selected 2D endpoint (the "second-best match"). For example, if each similarity metric is normalized such that 0 represents no similarity and 1 represents perfect similarity, then a confidence match value may be computed as the difference between 1 and the quotient of the second highest similarity metric to the highest similarity metric. In this way, if one candidate pixel block stands out as being a clear best match (i.e., because it has a much higher similarity metric than the second-best match), the quotient will be nearly 0 and the match confidence value will be high (i.e., close to 1). Conversely, if the highest similarity metric is the same or only slightly better than the second-highest similarity metric (thereby indicating that no particular match stands out as clearly being the best match), the quotient will be at or near 1 and the match confidence value will be low (i.e., close to 0). This match confidence value, or an analogous value computed in another suitable manner, may be used to define the 3D endpoint (or to determine whether a 3D endpoint is to be defined at all) in any of the ways described herein.

In some examples, as mentioned above, it may not be desirable to define a 3D endpoint based on a user-selected 2D endpoint and a corresponding matched 2D endpoint that do not match with a suitably high confidence level. For example, the risk that such a 3D endpoint could be inaccurate and lead to an inaccurate measurement may be such that it would be preferable for system 600 to abstain from making the measurement at all rather than risk making an inaccurate measurement. In such examples, system 600 may indicate the failure to identify a match with a suitably high confidence level to the user and allow the user to try again to designate a user-selected 2D endpoint for which a corresponding matched 2D endpoint may be successfully identified. Additionally or alternatively, system 600 may be configured, in such situations, to automatically designate a 2D endpoint nearby the user-selected 2D endpoint (e.g., a 2D endpoint corresponding to a more easily identifiable feature) and to automatically reattempt to identify the matched 2D endpoint.

Specifically, for example, system 600 may identify a first matched 2D endpoint based on a user-selected 2D endpoint, and may determine a match confidence value for the first matched 2D endpoint is below a predetermined confidence threshold. As a result, system 600 may identify (e.g., based on the user-selected 2D endpoint and in response to the determination that the match confidence value is below the predetermined confidence threshold) a replacement 2D endpoint corresponding to the feature. The replacement 2D endpoint may be distinct from the user-selected 2D endpoint, but may be related to the user-selected 2D endpoint (e.g., in close proximity to the user-selected 2D endpoint). System 600 may then identify a second matched 2D endpoint corresponding to the feature as represented in the second image. This identification may be based on the user-selected 2D endpoint in the sense that it is based on the replacement 2D endpoint that itself was identified based on the user-selected 2D endpoint. System 600 may then define a 3D endpoint corresponding to the feature based on the user-selected 2D endpoint by defining the 3D endpoint based on the replacement 2D endpoint that was identified based on the user-selected 2D endpoint.

As discussed above, systems and methods described herein may provide various advantages of convenience and accuracy by measuring a distance using a stereoscopic endoscope rather than, for example, kinematic data for surgical instruments alone. However, in certain implementations, kinematic data may be combined with endoscopic image data to further improve the accuracy of anatomical measurements systems such as system 600. For example, system 600 may identify a matched 2D endpoint by tracking kinematics of one or more surgical instruments (e.g., one or more of surgical instruments 114, such as stereoscopic endoscope 500) located at the surgical area. System 600 may use the tracked kinematics to identify rectangular area 902 and/or analyze the candidate pixel blocks 1002 in order to assign similarity metrics to the candidate pixel blocks 1002.

Figure 11:
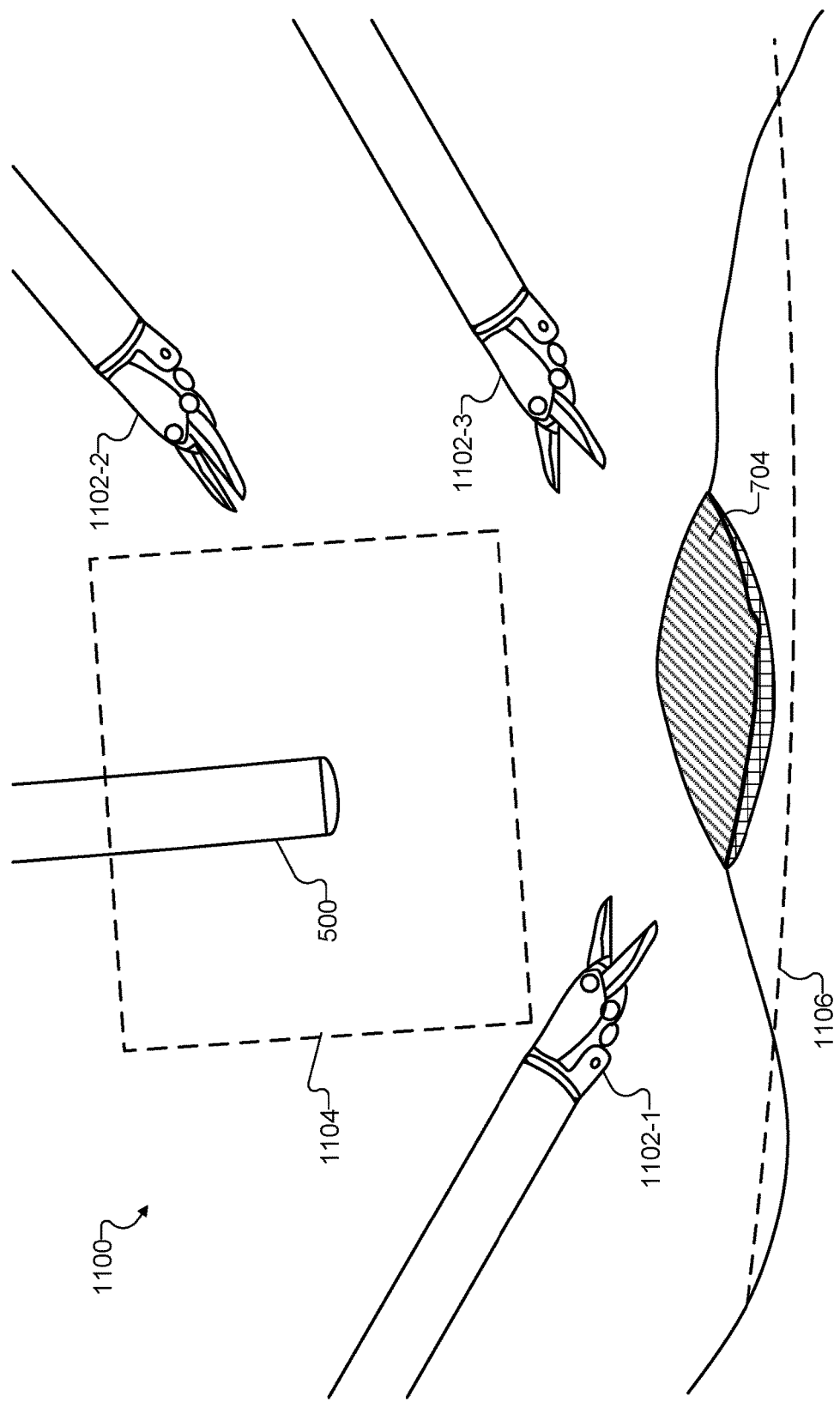
FIG. 11 illustrates a plurality of surgical instruments within a surgical area internal to a patient according to principles described herein.

To illustrate, FIG. 11 shows a side view 1100 of stereoscopic endoscope 500 along with surgical instruments 1102-1 through 1102-3 within the surgical area that includes hernia 704. Stereoscopic endoscope 500 may include any of the components described above (many of which are not explicitly shown in view 1100), and surgical instruments 1102 may implement any of the surgical instruments described herein (e.g., surgical instruments 114).

Because of inherent error that may be introduced and accumulate over the length of a kinematic chain, it may not be possible, based on kinematic data alone, to determine a precise position for the distal tip of stereoscopic endoscope 500. However, tracked kinematic data of the robotic arm to which stereoscopic endoscope 500 is coupled may provide enough data for system 600 to determine at least an approximate position of the distal tip of stereoscopic endoscope 500. For example, based on the tracked kinematic data alone, it may be determined that the distal tip is located somewhere within an area 1104. Additionally, while kinematic data alone may not indicate precise positions at which each surgical instrument 1102 is disposed, tracked kinematic data of the respective robotic arms to which each of surgical instruments 1102 is coupled may indicate a boundary 1106 beyond which surgical instruments 1102 have not been moved. However, because no surgical instrument 1102 has been detected to go beyond boundary 1106, boundary 1106 may be assumed to at least approximate a surface of tissue within the surgical area, especially as boundary 1106 becomes increasingly well defined as a surgical session proceeds and more kinematic data is tracked and acquired.

By defining and tracking kinematic data representative of area 1104, boundary 1106, and/or other such indications, system 100 may more accurately and successfully match user-selected 2D endpoints to matched 2D endpoints using the techniques described above. For instance, based exclusively on a relationship between area 1104 and boundary 1106 (i.e., based solely on tracked kinematic data), system 600 may approximate how far stereoscopic endoscope 500 is from a surface of hernia 704 at any particular time. This information, in turn, may be used to help determine the size of the rectangular area to be searched for a matched 2D endpoint to match to a particular user-selected 2D endpoint. For example, based on the distance between area 1104 and boundary 1106, system 600 may be able to reduce the size of the rectangular area without ruling out any area where the matched 2D endpoint is likely to be found. This may help avoid false positive matches and may increase efficiency since system 600 may have fewer candidate pixel blocks to analyze within a smaller rectangular area. Additionally or alternatively, the kinematic data represented by area 1104 and boundary 1106 may be used to eliminate false positive matches in other ways, to increase or decrease match confidence values assigned to identified matches, or to otherwise facilitate system 600 in efficiently identifying the most accurate matched 2D endpoint possible for a given user-selected 2D endpoint.

In some examples, information determined based on images detected by stereoscopic endoscope 500 may help verify or correct estimated instrument or anatomy positions that have been determined based on tracked kinematic data. For example, while area 1104 and/or boundary 1106 may be determined based on kinematic data alone, area 1104 may be made smaller and more accurate and boundary 1106 may be made to more closely conform to the actual tissue surface based on data derived from images captured by stereoscopic endoscope 500. As such, in certain examples, information determined by system 600 based on stereoscopic endoscope 500 may be fed back into a kinematic tracking system to correct and/or improve the precision of raw kinematic data being tracked.

Subsequent to a user designation of a user-selected 2D endpoint and a successful identification of a matched 2D endpoint corresponding to the user-selected 2D endpoint in any of the ways described above, system 600 may define a 3D endpoint based on the user-selected and matched 2D endpoints. The definition of the 3D endpoint may be performed in any suitable way, such as by using a triangulation technique based on epipolar geometry.

Figure 12:
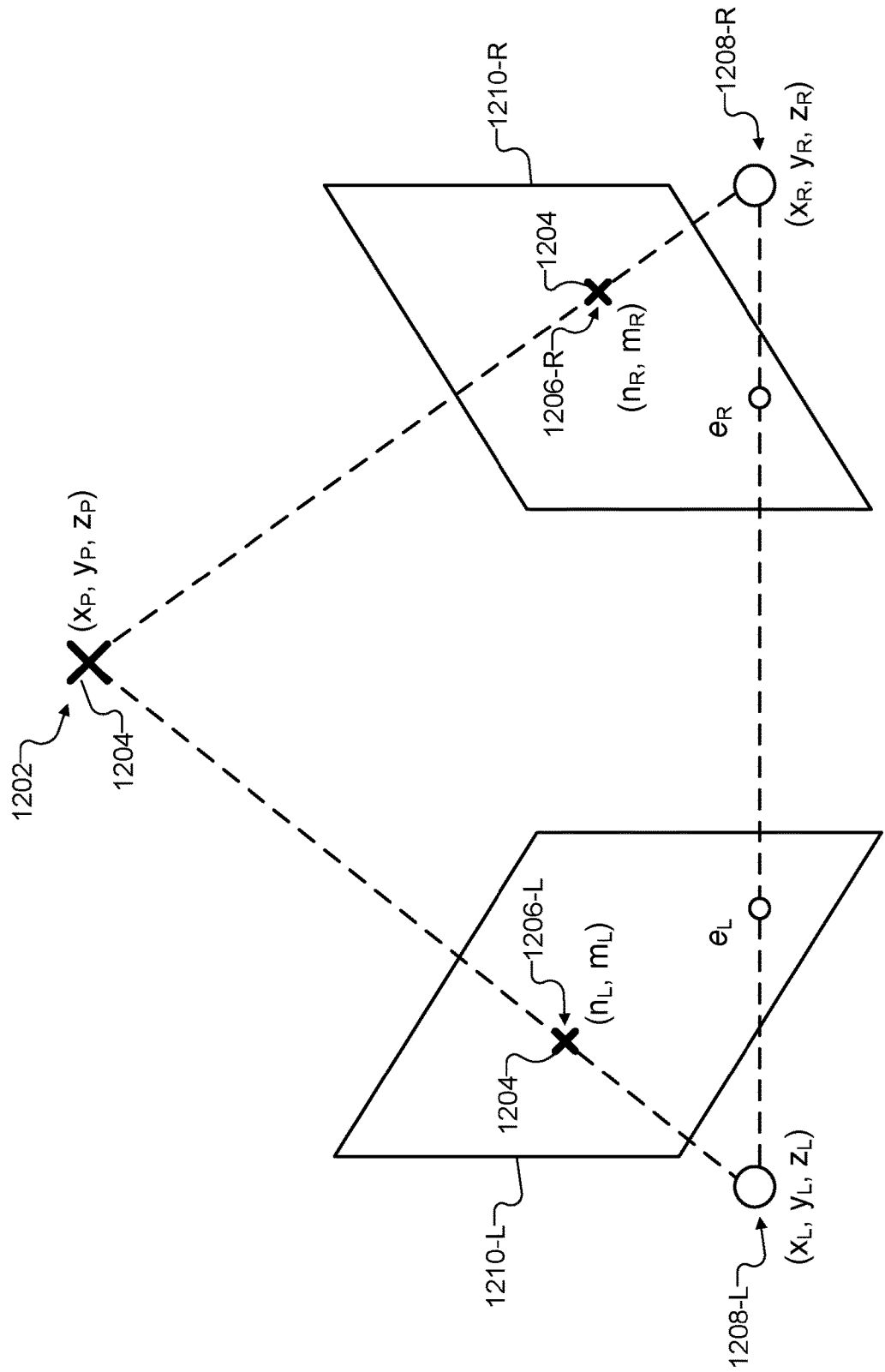
FIG. 12 illustrates an exemplary definition of a three-dimensional ("3D") endpoint according to principles described herein.

FIG. 12 illustrates an exemplary definition of a 3D endpoint 1202 corresponding to a feature 1204 (i.e., represented by an "X" shape). For example, the definition of 3D endpoint 1202 may be based on 2D endpoints 1206 (e.g., a user-selected 2D endpoint 1206-L and a corresponding matched 2D endpoint 1206-R). FIG. 12 shows various coordinates of the form "(x, y, z)" to illustrate 3D positions with respect to a coordinate system (e.g., a world coordinate system associated with robotic surgical system 100, a local coordinate system associated with a stereoscopic endoscope, or the like). For example, a vantage point 1208-L at $(x_L, y_L, z_L)$ may represent a known position from which a left-side camera of the stereoscopic endoscope captures a left-side image 1210-L, and a vantage point 1208-R at $(x_R, y_R, z_R)$ may represent a known position from which a right-side camera of the stereoscopic endoscope captures a right-side image 1210-R. 3D endpoint 1202 at $(x_P, y_P, z_P)$ may represent the 3D endpoint that system 600 is to define based on the known positions of vantage points 1208-L and 1208-R and based on respective representations of feature 1204 represented in both images 1210-L and 1210-R. Specifically, as shown, user-selected 2D endpoint 1206-L may mark feature 1204 at 2D coordinates $(n_L, m_L)$ of image 1210-L while matched 2D endpoint 1206-R may mark feature 1204 at 2D coordinates $(n_R, m_R)$ of image 1210-R.

Also identified in images 1210-L and 1210-R are respective epipoles $e_L$ and $e_R$ which may represent, within each image 1210, the location of the opposite vantage point 1208. The relative positions of the respective epipoles, as well as other suitable intrinsic or extrinsic parameters defining the left-side and right-side cameras (e.g., a distance between vantage points 1208, a focal point of each camera, etc.), may be determined during a calibration process or in any other suitable manner. Then, based on the known positions of vantage points 1208 and their relationship to one another, as well as the positions of 2D endpoints 1206-L and 1206-R on images 1210-L and 1210-R, system 600 may triangulate the position of 3D endpoint 1202 using conventional epipolar geometry.

Using the operations described above and/or any other suitable operations, a user-selected 2D endpoint may be matched to a stereoscopic matched 2D endpoint and triangulated to define a corresponding 3D endpoint such as 3D endpoint 1202. Once at least two such 3D endpoints are defined, system 600 may calculate a distance in space from one 3D endpoint to the other within the coordinate system in which the 3D endpoints are defined.

While operations for selecting and deriving a first 3D endpoint have been described above in detail, it will be understood that an additional 3D endpoint must also be defined in order to determine a distance from the first 3D endpoint (e.g., 3D endpoint 1202) to the additional 3D endpoint. To this end, the additional 3D endpoint may be defined in any suitable way. For example, system 600 may define the additional 3D endpoint in the same way that the first 3D endpoint was defined. That is, system 600 may receive (e.g., from the same user who provided user input designating the first user-selected 2D endpoint) user input designating an additional user-selected 2D endpoint corresponding to an additional feature as represented in image 702-L, identify (e.g., based on the additional user-selected 2D endpoint) an additional matched 2D endpoint corresponding to the additional feature as represented in image 702-R, and define (e.g., based on the additional user-selected and matched 2D endpoints) the additional 3D endpoint corresponding to the additional feature. Each of these operations may be performed in any of the ways described herein.

In other examples, the additional 3D endpoint may be selected or defined in a different manner. Specifically, for instance, the additional 3D endpoint may be associated with a position of a known location such as a position of a surgical instrument, a position of an endoscope, an origin point of a coordinate system, or the like. In these examples, it thus may not be necessary for a user to designate the additional user-selected 2D endpoint based on a feature presented in a 2D image. Instead, the user may indicate that the additional 3D endpoint corresponds to the particular surgical instrument, endoscope, origin point, or other known location in any suitable way.

Figure 13:
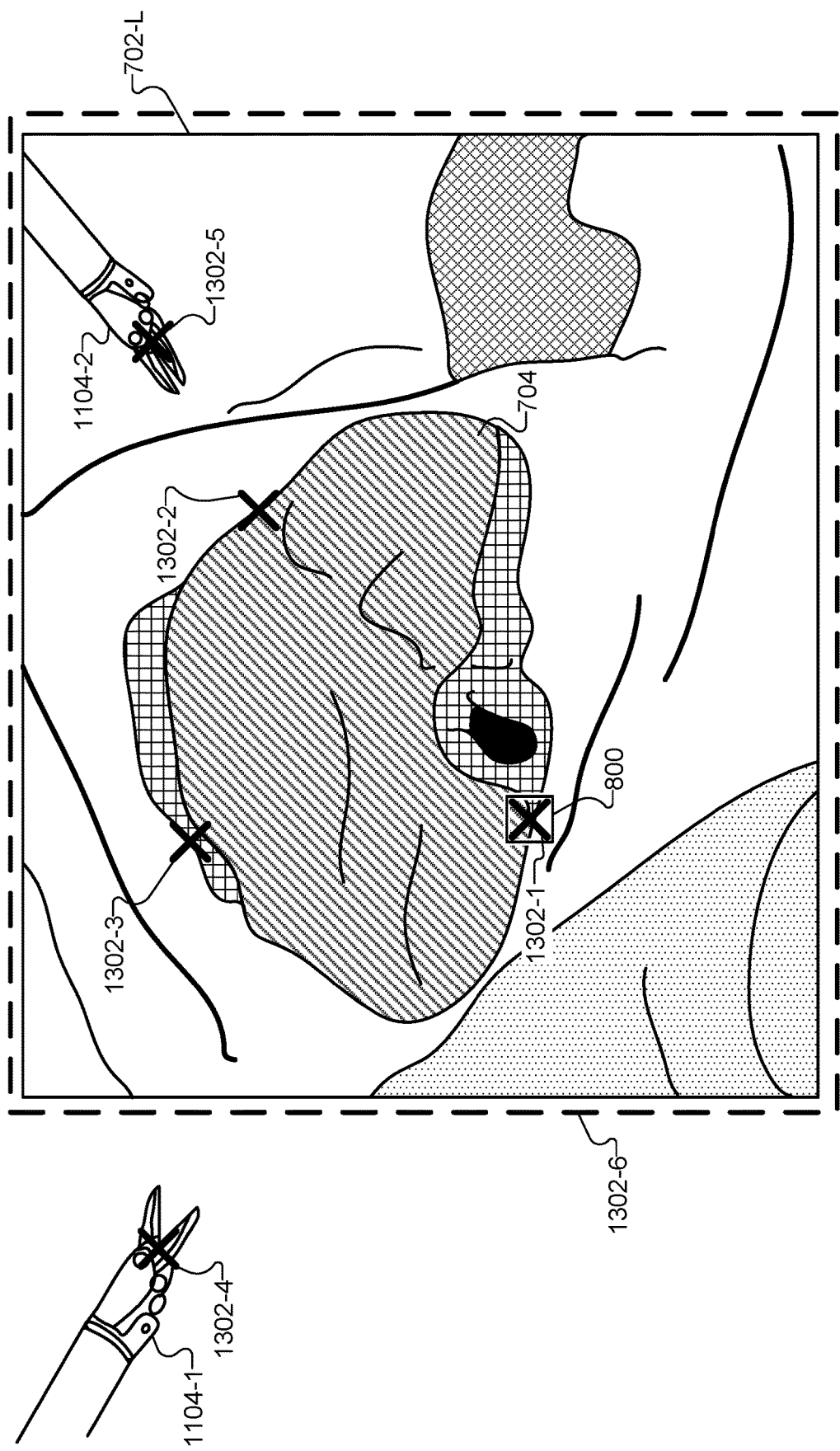
FIG. 13 illustrates exemplary 3D endpoints between which one or more distances may be determined according to principles described herein.

To illustrate, FIG. 13 illustrates exemplary 3D endpoints 1302 (e.g., 3D endpoints 1302-1 through 1302-6) between which one or more distances may be determined. As shown in FIG. 13, a first 3D endpoint 1302-1 defined based on user-selected 2D endpoint 800 within image 702-L may be positioned at a first edge of hernia 704. Once this first 3D endpoint 1302-1 is defined based on user-selected 2D endpoint 800, a distance may be determined from 3D endpoint 1302-1 to any additional 3D endpoint represented by 3D endpoints 1302-2 through 1302-6. For instance, a distance from one edge to another of hernia 704 may be determined by determining a distance between 3D endpoint 1302-1 and one of 3D endpoints 1302-2 and 1302-3.

In other examples, the additional feature to which the additional 3D endpoint 1302 corresponds may be a non-anatomical feature (i.e., a feature included within the surgical area that is not part of the patient's anatomy). For instance, 3D endpoint 1302-4 may be associated with a tip of surgical instrument 1104-1, which is not currently represented within image 702-L but may still be within the surgical area. As another example, 3D endpoint 1302-5 may be associated with a tip of surgical instrument 1104-2, which is represented within image 702-L. As yet another example, 3D endpoint 1302-6 may be associated with a tip of stereoscopic endoscope 500 (depicted as a dotted line around image 702-L). In examples where a non-anatomical feature to which a 3D endpoint corresponds is not represented within image 702-L (e.g., for the features to which 3D endpoints 1302-4 and 1302-6 correspond), kinematic data may be used to determine the coordinates of the 3D endpoint 1302. Kinematic and/or endoscopic image data may be used to determine the coordinates of non-anatomical features that are represented within image 702-L, such as the coordinates of 3D endpoint 1302-5.

In examples where a distance to be determined is from an anatomical feature to a non-anatomical feature such as a surgical instrument 1104 hovering above the anatomical feature, it may be useful to measure a direct point-to-point distance between the two 3D endpoints. However, in various other examples such as those involving 3D endpoints associated with two anatomical features, it may be desirable to measure a contoured distance from one 3D endpoint to the other along the contours of the tissue (i.e., rather than directly through the tissue). For instance, in the example described above in which a distance across hernia 704 is to be measured so that a mesh patch may be cut to an appropriate size, it may be desirable to determine the distance across hernia 704 along the surface of hernia 704 rather determining the distance passing directly through hernia 704.

Figure 14:
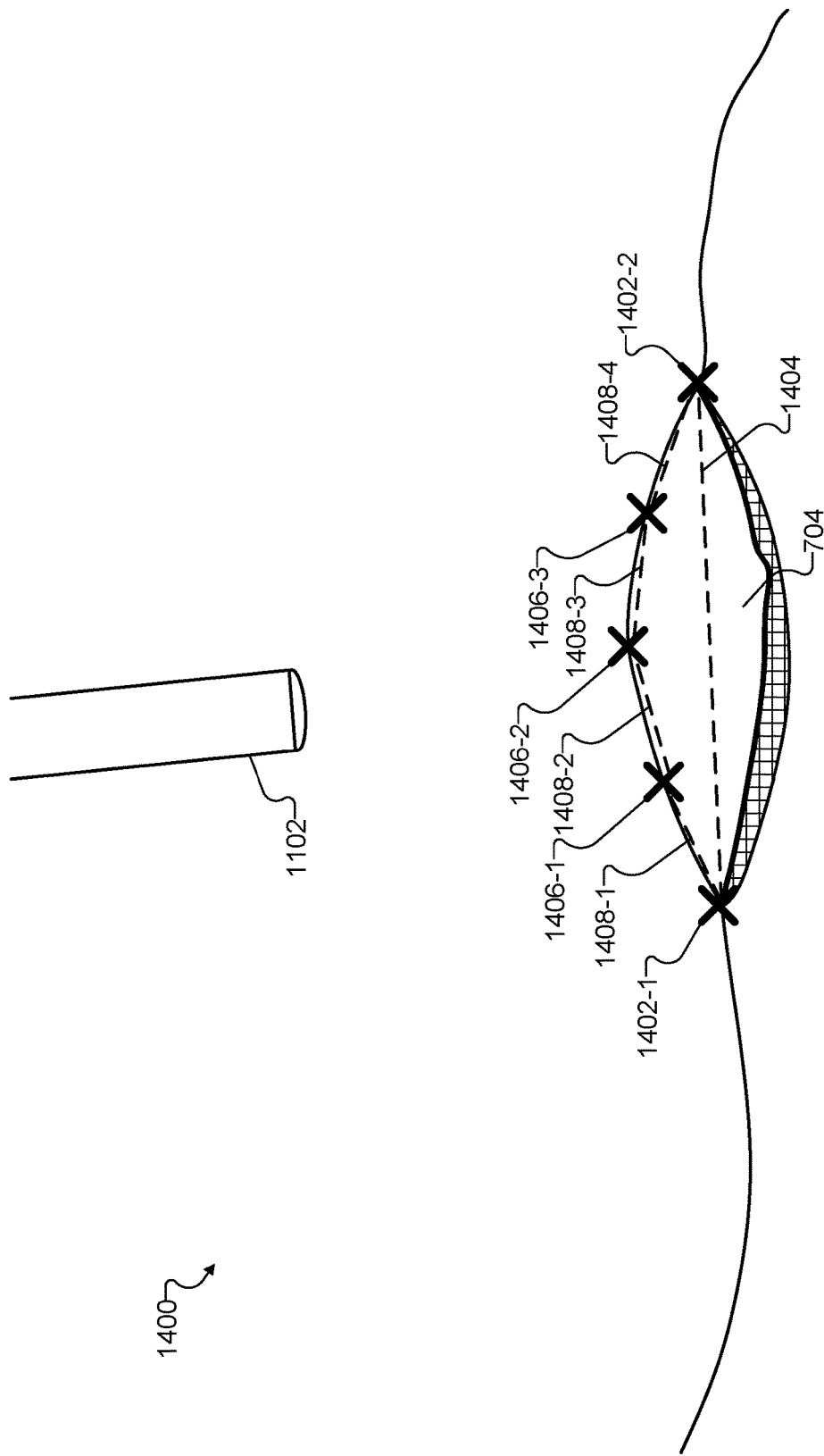
FIG. 14 illustrates an exemplary contoured distance between two 3D endpoints according to principles described herein.

To illustrate, FIG. 14 shows exemplary aspects of how a contoured distance from one 3D endpoint to an additional 3D endpoint may be estimated. Specifically, as shown in a side view 1400, 3D endpoints 1402-1 and 1402-2 (collectively referred to as "3D endpoints 1402") may be located at opposite edges of hernia 704. For example, 3D endpoint 1402-1 may implement 3D endpoint 1302-1, while 3D endpoint 1402-2 may implement one of 3D endpoints 1302-2 or 1302-3. In FIG. 14, a direct point-to-point distance 1404 is drawn between 3D endpoints 1402, passing directly through tissue of hernia 704. While point-to-point distance 1404 may be useful in certain contexts, it may not be an ideal distance to use for sizing a mesh patch to cover hernia 704, since the mesh patch will need to cover the surface of hernia 704. Accordingly, it may be desirable to determine a distance over the surface of hernia 704, which may be referred to herein as a "contoured distance" over the tissue.

To determine this contoured distance, system 600 may automatically identify one or more 3D midpoints 1406 (e.g., 3D midpoints 1406-1 through 1406-3 and/or additional 3D midpoints not explicitly shown) on a 3D contour that connects the 3D endpoint to the additional 3D endpoint and that runs along a physical surface upon which the 3D endpoint and the additional 3D endpoint are both disposed (i.e., the outer surface of hernia 704). System 600 may then determine, based on 3D midpoints 1406, intermediate distances 1408 (e.g., intermediate distances 1408-1 through 1408-4) for each segment of a linearly-segmented route from 3D endpoint 1402-1 to 3D endpoint 1402-2 that passes through each adjacent 3D midpoint 1406 so as to substantially adhere to the 3D contour between 3D endpoints 1402. Based on intermediate distances 1408, system 600 may compute the contoured distance from 3D endpoint 1402-1 to 3D endpoint 1402-2 as a sum of intermediate distances 1408. The sum of intermediate distances 1408 may provide an estimation for an exact contoured distance that becomes more accurate as more 3D midpoints 1406 and more intermediate distances 1408 are defined.

In some examples, a user may define 3D midpoints 1406 manually (e.g., by selecting 2D midpoints point by point) or may define a 2D line along which 3D midpoints 1406 are to be defined. For example, a touch screen may be used to draw a line along anatomy presented on the touch screen (e.g., from one side to the other of hernia 704) to designate user-selected 2D endpoints as well as midpoints between them. When midpoints are designated in this way or in another suitable manner (e.g., automatically by system 600), system 600 may estimate a contoured distance between the endpoints by estimating a distance along the contours of tissue connecting the endpoints by way of the midpoints. In other examples, other types of user interfaces such as pointer-based interfaces may be employed to achieve a similar result.

Figure 15:
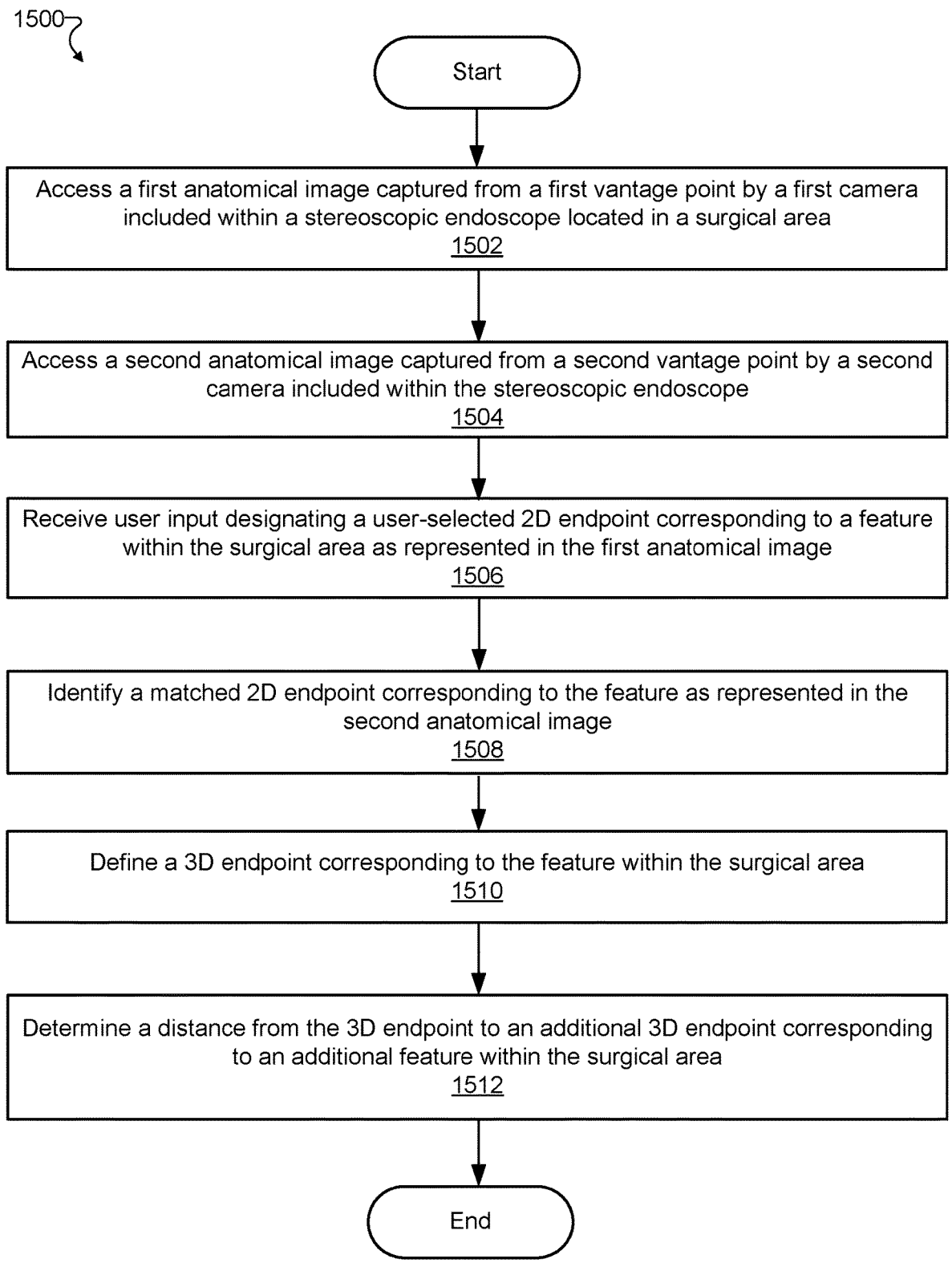
FIG. 15 illustrates an exemplary method for measuring a distance using a stereoscopic endoscope according to principles described herein.

FIG. 15 illustrates an exemplary method 1500 for measuring a distance using a stereoscopic endoscope. While FIG. 15 illustrates exemplary operations according to one embodiment, other embodiments may omit, add to, reorder, and/or modify any of the operations shown in FIG. 15. One or more of the operations shown in FIG. 15 may be performed by a measurement system such as system 600, any components included therein, and/or any implementation thereof.

In operation 1502, a measurement system may access a first image. For example, the accessed first image may be captured from a first vantage point by a first camera included within a stereoscopic endoscope located at a surgical area associated with a patient. Operation 1502 may be performed in any of the ways described herein.

In operation 1504, the measurement system may access a second image. For example, the accessed second image may be captured from a second vantage point by a second camera included within the stereoscopic endoscope. The second vantage point may be stereoscopic to the first vantage point from which the first image is captured by the first camera. Operation 1504 may be performed in any of the ways described herein.

In operation 1506, the measurement system may receive user input designating a user-selected 2D endpoint corresponding to a feature within the surgical area as represented in the first image. For example, the measurement system may receive the user input from a user of the measurement system such as a member of a surgical team involved with a surgical procedure being performed on the patient. Operation 1506 may be performed in any of the ways described herein.

In operation 1508, the measurement system may identify a matched 2D endpoint corresponding to the feature as represented in the second image. For example, the measurement system may identify the matched 2D endpoint based on the user-selected 2D endpoint determined to have been designated by the user in operation 1506. Operation 1508 may be performed in any of the ways described herein.

In operation 1510, the measurement system may define a 3D endpoint corresponding to the feature within the surgical area. For example, the measurement system may define the 3D endpoint based on the user-selected 2D endpoint determined to be designated in operation 1506 and the matched 2D endpoint identified in operation 1508. Operation 1510 may be performed in any of the ways described herein.

In operation 1512, the measurement system may determine a distance from the 3D endpoint to an additional 3D endpoint corresponding to an additional feature within the surgical area. Operation 1512 may be performed in any of the ways described herein.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 16:
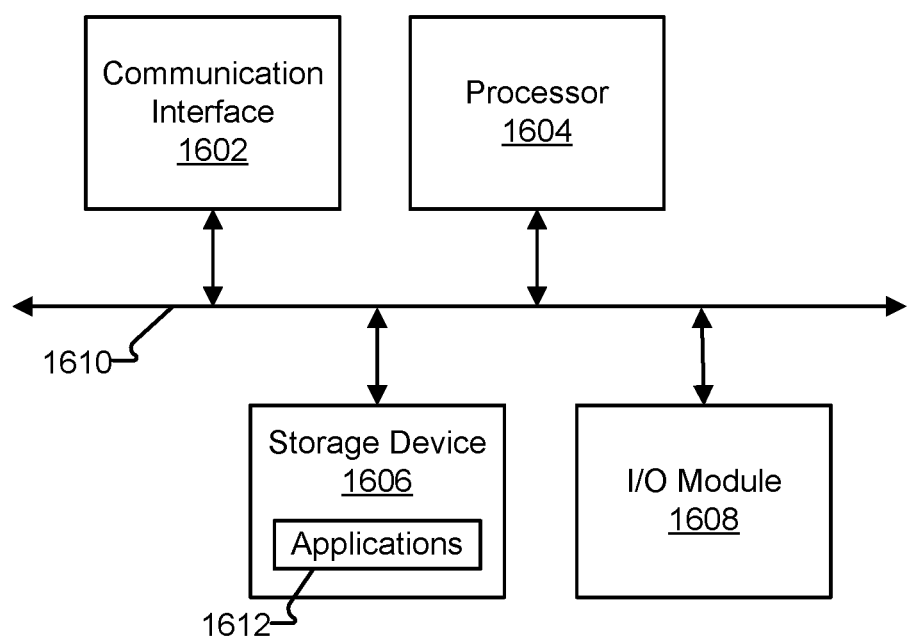
FIG. 16 illustrates an exemplary computing system according to principles described herein.

FIG. 16 illustrates an exemplary computing device 1600 that may be specifically configured to perform one or more of the processes described herein. As shown in FIG. 16, computing device 1600 may include a communication interface 1602, a processor 1604, a storage device 1606, and an input/output ("I/O") module 1608 communicatively connected via a communication infrastructure 1610. While an exemplary computing device 1600 is shown in FIG. 16, the components illustrated in FIG. 16 are not intended to be limiting. Additional or alternative components may be used in other embodiments. Components of computing device 1600 shown in FIG. 16 will now be described in additional detail.

Communication interface 1602 may be configured to communicate with one or more computing devices. Examples of communication interface 1602 include, without limitation, a wired network interface (such as a network interface card), a wireless network interface (such as a wireless network interface card), a modem, an audio/video connection, and any other suitable interface.

Processor 1604 generally represents any type or form of processing unit capable of processing data or interpreting, executing, and/or directing execution of one or more of the instructions, processes, and/or operations described herein. Processor 1604 may direct execution of operations in accordance with one or more applications 1612 or other computer-executable instructions such as may be stored in storage device 1606 or another computer-readable medium.

Storage device 1606 may include one or more data storage media, devices, or configurations and may employ any type, form, and combination of data storage media and/or device. For example, storage device 1606 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1606. For example, data representative of one or more executable applications 1612 configured to direct processor 1604 to perform any of the operations described herein may be stored within storage device 1606. In some examples, data may be arranged in one or more databases residing within storage device 1606.

I/O module 1608 may include one or more I/O modules configured to receive user input and provide user output. One or more I/O modules may be used to receive input for a single virtual reality experience. I/O module 1608 may include any hardware, firmware, software, or combination thereof supportive of input and output capabilities. For example, I/O module 1608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1608 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1600. For example, one or more applications 1612 residing within storage device 1606 may be configured to direct processor 1604 to perform one or more processes or functions associated facilities 602 through 606 of system 600. Likewise, storage facility 608 of system 600 may be implemented by storage device 1606 or a component thereof.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A measurement system comprising:
at least one physical computing device that
accesses a first image captured from a first vantage point by a first camera included within a stereoscopic endoscope located at a surgical area associated with a patient;
accesses a second image captured from a second vantage point by a second camera included within the stereoscopic endoscope, the second vantage point stereoscopic to the first vantage point;
receives, from a user of the measurement system, user input designating a user-selected two-dimensional ("2D") endpoint corresponding to a feature within the surgical area as represented in the first image;
identifies, based on the user-selected 2D endpoint, a matched 2D endpoint corresponding to the feature as represented in the second image;
defines, based on the user-selected and matched 2D endpoints, a three-dimensional ("3D") endpoint corresponding to the feature within the surgical area; and
determines a distance from the 3D endpoint to an additional 3D endpoint corresponding to an additional feature within the surgical area.

2. The measurement system of claim 1, wherein the at least one physical computing device further:
receives, from the user prior to determining the distance, user input designating an additional user-selected 2D endpoint corresponding to the additional feature as represented in the first image;
identifies, based on the additional user-selected 2D endpoint, an additional matched 2D endpoint corresponding to the additional feature as represented in the second image; and
defines, based on the additional user-selected and matched 2D endpoints, the additional 3D endpoint corresponding to the additional feature.

3. The measurement system of claim 1, wherein:
the user-selected 2D endpoint is a pixel block including a first number of rows and a first number of columns; and
the at least one physical computing device identifies the matched 2D endpoint by:
identifying, within the second image, a rectangular area including a plurality of candidate pixel blocks each including the first number of rows and the first number of columns, the rectangular area including a second number of pixels rows greater than the first number of rows and a second number of columns greater than the first number of columns and at least two times greater than the second number of rows;
analyzing the candidate pixel blocks in the plurality of candidate pixel blocks included within the rectangular area to assign, to each of the candidate pixel blocks, a respective similarity metric with respect to the user-selected 2D endpoint; and
based on the analyzing, identifying as the matched 2D endpoint corresponding to the feature a particular candidate pixel block that is assigned a highest similarity metric of the respective similarity metrics assigned to the analyzed candidate pixel blocks in the plurality of candidate pixel blocks.

4. The measurement system of claim 3, wherein the at least one physical computing device further identifies the matched 2D endpoint by:

tracking kinematics of at least one of the stereoscopic endoscope located at the surgical area and a robotically-manipulated surgical instrument located at the surgical area; and performing at least one of the identifying of the rectangular area including the plurality of candidate pixel blocks and the analyzing of the candidate pixel blocks to assign the respective similarity metrics to the candidate pixel blocks based on the tracked kinematics.

5. The measurement system of claim 3, wherein the respective similarity metric assigned to each individual candidate pixel block in the plurality of candidate pixel blocks is based on at least one of a sum of absolute differences between each pixel in the individual candidate pixel block and a corresponding pixel in the pixel block of the user-selected 2D endpoint;

a sum of squared differences between each pixel in the individual candidate pixel block and the corresponding pixel of the pixel block of the user-selected 2D endpoint;

a normalized cross correlation between each pixel in the individual candidate pixel block and the corresponding pixel of the pixel block of the user-selected 2D endpoint;

a census transformation;

a rank transformation; and a sum of absolute differences between horizontal and vertical gradients.

6. The measurement system of claim 1, wherein:

subsequent to the identification of the matched 2D endpoint corresponding to the feature as represented in the second image and prior to the definition of the 3D endpoint corresponding to the feature, the at least one physical computing device further:

identifies, based on the matched 2D endpoint, a reverse-matched 2D endpoint corresponding to the feature as represented in the first image, and determines, based on the user-selected and reverse-matched 2D endpoints, a match confidence value for the matched 2D endpoint; and the definition of the 3D endpoint corresponding to the feature is further based on the match confidence value for the matched 2D endpoint.

7. The measurement system of claim 1, wherein the at least one physical computing device receives the user input designating the user-selected 2D endpoint from the user by providing the first image for display on a monoscopic display screen communicatively coupled with the at least one physical computing device and configured to be used by an assistant to a surgeon associated with a surgical procedure performed on the patient; and receiving the user input as the user input is detected by a user interface associated with the display screen.

8. The measurement system of claim 1, wherein the at least one physical computing device receives the user input designating the user-selected 2D endpoint from the user by providing the first image for display on each display screen in a stereoscopic pair of display screens communicatively coupled with the at least one physical computing device and configured for use by a surgeon associated with a surgical procedure performed on the patient; and receiving the user input as the user input is detected by a user interface associated with the stereoscopic pair of display screens.

9. The measurement system of claim 1, wherein the at least one physical computing device receives the user input designating the user-selected 2D endpoint from the user by providing the first image for display on a display screen communicatively coupled with the at least one physical computing device;

providing a user interface associated with the display screen, the user interface including a pointer object configured to be moved by the user to any point on the display screen; and receiving the user input designating the user-selected 2D endpoint as a user selection of a particular point on the display screen to which the user has moved the pointer object.

10. The measurement system of claim 9, wherein the user selection of the particular point is performed dynamically by the movement of the pointer object to the particular point on the display screen without any additional user selection action.

11. The measurement system of claim 1, wherein the at least one physical computing device determines the distance from the 3D endpoint to the additional 3D endpoint by:

automatically identifying one or more 3D midpoints on a 3D contour that connects the 3D endpoint to the additional 3D endpoint and that runs along a physical surface upon which the 3D endpoint and the additional 3D endpoint are both disposed;

determining, based on the one or more 3D midpoints, intermediate distances for each segment of a linearly-segmented route from the 3D endpoint to the additional 3D endpoint that passes through each adjacent 3D midpoint so as to substantially adhere to the 3D contour between the 3D endpoint and the additional 3D endpoint; and determining the distance to be a contoured distance from the 3D endpoint to the additional 3D endpoint computed as a sum of the intermediate distances.

12. The measurement system of claim 1, wherein:

prior to the identification of the matched 2D endpoint corresponding to the feature as represented in the second image, the at least one physical computing device further:

identifies, based on the user-selected 2D endpoint, a low-confidence matched 2D endpoint, determines a match confidence value for the low-confidence matched 2D endpoint, determines that the match confidence value is below a predetermined confidence threshold, and identifies, based on the user-selected 2D endpoint and in response to the determination that the match confidence value is below the predetermined confidence threshold, a replacement 2D endpoint corresponding to the feature, the replacement 2D endpoint distinct from the user-selected 2D endpoint;

the identification of the matched 2D endpoint corresponding to the feature as represented in the second image is based on the user-selected 2D endpoint by being based on the replacement 2D endpoint that is identified based on the user-selected 2D endpoint; and the definition of the 3D endpoint corresponding to the feature is based on the user-selected 2D endpoint by being based on the replacement 2D endpoint that is identified based on the user-selected 2D endpoint.

13. The measurement system of claim 1, wherein both the feature and the additional feature are anatomical features within the patient.

14. The measurement system of claim 1, wherein the feature is an anatomical feature and the additional feature is a non-anatomical feature.

15. A measurement system comprising:
a stereoscopic endoscope configured to be located at a surgical area associated with a patient, the stereoscopic endoscope including
a first camera configured to capture a first image from a first vantage point, and
a second camera configured to capture a second image from a second vantage point that is stereoscopic to the first vantage point;
a display screen configured to display the first image;
a user interface associated with the display screen and allowing a user of the measurement system to designate, from a display of the first image on the display screen, a user-selected two-dimensional ("2D") endpoint corresponding to a feature within the surgical area as represented in the first image; and
at least one physical computing device communicatively coupled to the stereoscopic endoscope, the display screen, and the user interface, and configured to
identify, based on the user-selected 2D endpoint, a matched 2D endpoint corresponding to the feature as represented in the second image,
define, based on the user-selected and matched 2D endpoints, a three-dimensional ("3D") endpoint corresponding to the feature within the surgical area, and
determine a distance from the 3D endpoint to an additional 3D endpoint corresponding to an additional feature within the surgical area.

16. The measurement system of claim 15, wherein:
the user interface further allows the user to designate, from the display of the first image on the display screen, an additional user-selected 2D endpoint corresponding to the additional feature as represented in the first image;
the at least one physical computing device is further configured to
identify, based on the additional user-selected 2D endpoint, an additional matched 2D endpoint corresponding to the additional feature as represented in the second image, and
define, based on the additional user-selected and matched 2D endpoints, the additional 3D endpoint corresponding to the additional feature.

17. The measurement system of claim 15, wherein:
the user-selected 2D endpoint is a pixel block including a first number of rows and a first number of columns; and
the at least one physical computing device is configured to identify the matched 2D endpoint by:
tracking kinematics of at least one of the stereoscopic endoscope located at the surgical area and a robotically-manipulated surgical instrument located at the surgical area;
identifying, within the second image and based on the tracked kinematics, a rectangular area including a plurality of candidate pixel blocks each including the first number of rows and the first number of columns, the rectangular area including a second number of rows greater than the first number of rows and a second number of columns greater than the first number of columns and at least two times greater than the second number of rows;
analyzing, the candidate pixel blocks in the plurality of candidate pixel blocks included within the rectangular area to assign, to each of the candidate pixel blocks, a respective similarity metric with respect to the user-selected 2D endpoint; and
based on the analyzing, identifying as the matched 2D endpoint corresponding to the feature a particular candidate pixel block that is assigned a highest similarity metric of the respective similarity metrics assigned to the analyzed candidate pixel blocks in the plurality of candidate pixel blocks.

18. A method comprising:
accessing, by a measurement system, a first image captured from a first vantage point by a first camera included within a stereoscopic endoscope located at a surgical area associated with a patient;
accessing, by the measurement system, a second image captured from a second vantage point by a second camera included within the stereoscopic endoscope, the second vantage point stereoscopic to the first vantage point;
receiving, by the measurement system from a user of the measurement system, user input designating a user-selected two-dimensional ("2D") endpoint corresponding to a feature within the surgical area as represented in the first image;
identifying, by the measurement system based on the user-selected 2D endpoint, a matched 2D endpoint corresponding to the feature as represented in the second image;
defining, by the measurement system based on the user-selected and matched 2D endpoints, a three-dimensional ("3D") endpoint corresponding to the feature within the surgical area; and
determining, by the measurement system, a distance from the 3D endpoint to an additional 3D endpoint corresponding to an additional feature within the surgical area.

19. The method of claim 18, further comprising:
receiving, by the measurement system from the user prior to determining the distance, user input designating an additional user-selected 2D endpoint corresponding to the additional feature as represented in the first image;
identifying, by the measurement system based on the additional user-selected 2D endpoint, an additional matched 2D endpoint corresponding to the additional feature as represented in the second image; and
defining, by the measurement system based on the additional user-selected and matched 2D endpoints, the additional 3D endpoint corresponding to the additional feature.

20. The method of claim 18, wherein:
the user-selected 2D endpoint is a pixel block including a first number of rows and a first number of columns; and
the identifying of the matched 2D endpoint includes:
tracking kinematics of at least one of the stereoscopic endoscope located at the surgical area and a robotically-manipulated surgical instrument located at the surgical area;
identifying, within the second image and based on the tracked kinematics, a rectangular area including a plurality of candidate pixel blocks each including the first number of rows and the first number of columns, the rectangular area including a second number of rows greater than the first number of rows and a second number of columns greater than the first number of columns and at least two times greater than the second number of rows;

analyzing, the candidate pixel blocks in the plurality of candidate pixel blocks included within the rectangular area to assign, to each of the candidate pixel blocks, a respective similarity metric with respect to the user-selected 2D endpoint; and based on the analyzing, identifying as the matched 2D endpoint corresponding to the feature a particular candidate pixel block that is assigned a highest similarity metric of the respective similarity metrics assigned to the analyzed candidate pixel blocks in the plurality of candidate pixel blocks.

* * * * *